United States Patent
King et al.

(10) Patent No.: US 9,283,262 B2
(45) Date of Patent: Mar. 15, 2016

(54) PREDICTING AND TREATING DIABETIC COMPLICATIONS

(75) Inventors: George L. King, Dover, MA (US); Hillary A. Keenan, Watertown, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 13/992,149

(22) PCT Filed: Dec. 6, 2011

(86) PCT No.: PCT/US2011/063514
§ 371 (c)(1),
(2), (4) Date: Oct. 30, 2013

(87) PCT Pub. No.: WO2012/078618
PCT Pub. Date: Jun. 14, 2012

(65) Prior Publication Data
US 2014/0187498 A1    Jul. 3, 2014

Related U.S. Application Data

(60) Provisional application No. 61/420,686, filed on Dec. 7, 2010.

(30) Foreign Application Priority Data

Aug. 4, 2011 (WO) ................ PCT/US2011/046672

(51) Int. Cl.
*C12Q 1/68* (2006.01)
*G01N 33/53* (2006.01)
*A61K 38/17* (2006.01)

(52) U.S. Cl.
CPC .......... *A61K 38/1709* (2013.01); *C12Q 1/6883* (2013.01); *C12Q 2600/118* (2013.01); *C12Q 2600/158* (2013.01); *G01N 2800/042* (2013.01); *G01N 2800/164* (2013.01); *G01N 2800/347* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2003/0161859 A1    8/2003    Gardner et al.
2010/0150920 A1    6/2010    Glaser

FOREIGN PATENT DOCUMENTS

WO    03/079968 A2    10/2003

OTHER PUBLICATIONS

Garcia-Ramirez et al., "Interphotoreceptor retinoid-binding protein (IRBP) is downregulated at early stages of diabetic retinopathy," Diabetologia 52:2633-41(Oct. 13, 2009).*
Sasamoto et al., "Immunomodulation of experimental autoimmune uveoretinitis by intravenous injection of uveitogenic peptides," Invest. Ophthal. Visual Sci. 33:2641-2649 (1992).*
Gao, et al., "Characterization of the Vitreous Proteome in Diabetes without Diabetic Retinopathy and Diabetes with Proliferative Diabetic Retinopathy" Journal of Proteome Research, vol. 7, 2008, pp. 2516-2525.
Koopman, et al., "Changes in Age at Diagnosis of Type 2 Diabetes Mellitus in the United States, 1988 to 2000" Annals of Family Medicine, vol. 3, No. 1, Jan./Feb. 2005, pp. 60-63.
Datta, et al., "Effect of GSTM1 and GSTT1 double deletions in the development of oxidative stress in diabetic nephropathy patients" Indian Journal of Biochemistry & Biophysics, vol. 47, Apr. 2010, pp. 100-103.
Li, et al., "Proteomic profile of primary isolated rat mesangial cells in high-glucose culture condition and decreased expression of PSMA6 in renal cortex of diabetic rats", Biochem. Cell Biol., vol. 88, Jun. 2010, pp. 635-648.
Yamane, et al., "Proteome Analysis of Human Vitreous Proteins", Molecular & Cellular Proteomics, vol. 2, No. 11, Sep. 2003, pp. 1177-1187.
Pai, et al. "Current concepts in intravitreal drug therapy for diabetic retinopathy" Saudi Journal of Ophthalmology; 2010; vol. 24; pp. 143-149.
Garcia-Ramirez, et al. "Interphotoreceptor retinoid-binding protein (IRBP) is downregulated at early stages of diabetic retinopathy" Diabetologia; 2009; vol. 52; pp. 2633-2641.
Lin, et al. "Biochemical and Biophysical Properties of Recombinant Human Interphotoreceptor Retinoid Binding Protein" Investigative Ophthalmology & Visual Science; Sep. 1994; vol. 95; Issue No. 10; pp. 3599-3612.
Simo, et al. "The Retinal Pigment Epithelium: Something more than a constituent of the blood-retinal barrier—Implications for the Pathogenesis of Diabetic Retinopathy" Journal of Biomedicine and Biotechnology; 2010; vol. 2010; 15 pages.

* cited by examiner

*Primary Examiner* — Julie Ha
*Assistant Examiner* — Kristina M Hellman
(74) *Attorney, Agent, or Firm* — Pierce Atwood LLP; Kevin M. Farrell; David J. Wilson

(57) ABSTRACT

Compositions and methods for diagnosing, predicting risk of, and/or treating diabetic retinopathy and/or diabetic nephropathy.

5 Claims, 17 Drawing Sheets

| Nephro Class | PDR | Sex | A1c (%) | Agedx (years) | Dur (years) | Cause of Death | HTN | ACR (mcg/mg) | eGFR (ml/min/1.73 m²) |
|---|---|---|---|---|---|---|---|---|---|
| I | Mild | F | 6.7 | 23 | 57 | MI | Y | 5.4 | 48.4 |
| I | Mod | M | 5.6 | 7 | 50 | Cancer | N | 4.3 | 82.0 |
| I | PDR | M | 6.6 | 4 | 72 | Cardiac arrest | Y | 3.5 | 47.2 |
| IIA | No | M | 7.2 | 16 | 72 | Organ failure | N | 18.3 | 67.9 |
| IIA | No | M | 7.1 | 27 | 51 | Cancer | No | 13.3 | 76.9 |
| IIA | Mild | M | 9.0 | 5 | 79 | Cardiac arrest | Y | 23.1 | 61.4 |
| IIA | Mild | F | 8.8 | 1 | 57 | Stroke | Y | 36.9 | 54.3 |
| IIA | PDR | F | 7.3 | 7 | 64 | Intra-cranial hemorrhage | Y | 39.3 | 44.9 |
| IIB | PDR | M | 7.3 | 10 | 75 | CHF | Y | 346.0 | 55.9 |
| IIB | PDR | F | 5.7 | 8 | 57 | Cancer | Y | 7.9 | 43.8 |
| III | PDR | F | 5.7 | 24 | 53 | Cancer | Y | 7.3 | 43.7 |
| III | PDR | F | 9.8 | 5 | 65 | Renal Failure | Y | 3619 | 26.2 |

FIG. 6

| Accession | Protein Name | Fold | p |
|---|---|---|---|
| IPI00009997 | B3GNT1: N-acetyllactosaminide beta-1,3-N-acetylglucosaminyltransferase | ∞ | 0.0067 |
| IPI00024292 | LRP2: Low-density lipoprotein receptor-related protein 2 precursor | ∞ | 0.0068 |
| IPI00029260 | CD14: Monocyte differentiation antigen CD14 precursor | ∞ | 0.0248 |
| IPI00554760 | TNR: Isoform 2 of Tenascin-R precursor | ∞ | 0.0252 |
| IPI00744685 | BTD: Uncharacterized protein BTD (Fragment) | ∞ | 0.0252 |
| IPI00783390 | CHL1: Isoform 1 of Neural cell adhesion molecule L1-like protein precursor | ∞ | 0.0067 |
| IPI00789259 | IGLV1: 40 V1-13 protein (Fragment) | ∞ | 0.0252 |
| IPI00022822 | COL18A1: Isoform 2 of Collagen alpha-1(XVIII) chain precursor | 16.80 | 0.0145 |
| IPI00748395 | SEZ6: Isoform 3 of Seizure protein 6 homolog precursor | 10.73 | 0.0143 |
| IPI00024284 | HSPG2: Basement membrane-specific heparan sulfate proteoglycan core protein precursor | 9.10 | 0.0360 |
| IPI00607600 | APLP1: amyloid precursor-like protein 1 isoform 1 precursor | 9.10 | 0.0181 |
| IPI00242956 | FCGBP: IgGFc-binding protein precursor | 7.55 | 0.0329 |
| IPI00031030 | APLP2: Isoform 1 of Amyloid-like protein 2 precursor | 6.75 | 0.0086 |
| IPI00216138 | TAGLN: Transgelin | 4.20 | 0.0373 |
| IPI00032220 | AGT: Angiotensinogen precursor | 3.39 | 0.0181 |
| IPI00022395 | C9: Complement component C9 precursor | 3.27 | 0.0138 |
| IPI00878576 | Autotaxin isoform gamma | 2.84 | 0.0416 |
| IPI00022337 | RBP3: Interphotoreceptor retinoid-binding protein precursor | 2.71 | 0.0045 |
| IPI00855916 | Transthyretin | 2.68 | 0.0424 |
| IPI00032293 | CST3: CST2 Cystatin-C precursor | 2.45 | 0.0424 |
| IPI00478003 | A2M: Alpha-2-macroglobulin precursor | 2.10 | 0.0284 |
| IPI00017601 | CP: Ceruloplasmin precursor | 1.58 | 0.0118 |

FIG. 7

| Protein Name | | Fold | p |
|---|---|---|---|
| IPI00789618 | HDDC3: Isoform 1 of HD domain-containing protein 3 | ∞ | 0.0102 |
| IPI00178926 | IGJ: immunoglobulin J chain | 23.63 | 0.0391 |
| IPI00816799 | Rheumatoid factor D5 light chain (Fragment) | 11.00 | 0.0391 |
| IPI00410215 | BPNT1: Isoform 2 of 3(2),5-bisphosphate nucleotidase 1 | 8.00 | 0.0385 |
| IPI00009305 | GNPDA1: Glucosamine-6-phosphate isomerase | 6.60 | 0.0206 |
| IPI00873466 | HPRT1: Uncharacterized protein HPRT1 | 4.09 | 0.0174 |
| IPI00893316 | GSTT1: Glutathione S-transferase theta 1 | 3.48 | 0.0319 |
| IPI00004101 | BHMT: Betaine--homocysteine S-methyltransferase 1 | 3.22 | 0.0335 |
| IPI00848298 | APOA1BP: Isoform 2 of Apolipoprotein A-1-binding protein precursor | 2.69 | 0.0115 |
| IPI00022488 | HPX: Hemopexin precursor | 2.44 | 0.0204 |
| IPI00218407 | ALDOB: Fructose-bisphosphate aldolase B | 2.36 | 0.0208 |
| IPI00305360 | AGMAT: Agmatinase, mitochondrial precursor | 2.35 | 0.0262 |
| IPI00792191 | GATM: Glycine amidinotransferase (L-arginine:glycine amidinotransferase) variant | 2.13 | 0.0208 |
| IPI00219446 | PEBP1: Phosphatidylethanolamine-binding protein 1 | 2.11 | 0.0332 |
| IPI00025366 | CS: Citrate synthase, mitochondrial precursor | 2.06 | 0.0204 |

```
   1 mmrewvllms vllcglagpt hlfqpslvld makvlldnyc fpenllgmqe aiqqaikshe
  61 ilsisdpqtl asvltagvqs slndprlvis yepstpeppp qvpaltslse eellawlqrg
 121 lrhevlegnv gylrvdsvpg qevlsmmgef lvahvwgnlm gtsalvldlr hctggqvsgi
 181 pyiisylhpg ntilhvdtiy nrpsntttei wtlpqvlger ygadkdvvvl tssqtrgvae
 241 diahilkqmr raivvgertg ggaldlrklr igesdffftv pvsrslgplg ggsqtwegsg
 301 vlpcvgtpae qalekalail tlrsalpgvv hclqevlkdy ytlvdrvptl lqhlasmdfs
 361 tvvseedlvt klnaglqaas edprllvrai gptetpswpa pdaaaedspg vapelpedea
 421 irqalvdsvf qvsvlpgnvg ylrfdsfada svlgvlapyv lrqvweplqd tehlimdlrh
 481 npggpssavp lllsyfggpe agpvhlftty drrtnitqeh fshmelpgpr ystqrgvyll
 541 tshrtataae efaflmqslg watlvgeita gnllhtrtvp lldtpegsla ltvpvltfid
 601 nhgeawlggg vvpdaivlae ealdkaqevl efhqslgalv egtghlleah yarpevvgqt
 661 sallraklaq gayrtavdle slasqltadl qevsgdhrll vfhspgelvv eeappppppav
 721 pspeeltyli ealfktevlp gqlgylrfda maeletvkav gpqlvrlvwq qlvdtaalvi
 781 dlrynpgsys taipllcsyf feaeprqhly svfdratskv tevwtlpqva gqrygshkdl
 841 yilmshtsgs aaeafahtmq dlqratvige ptaggalsvg iyqvgssply asmptqmams
 901 attgkawdla gvepditvpm sealsiaqdi valrakvptv lqtagklvad nyasaelgak
 961 matklsglqs rysrvtseva laeilgadlq mlsgdphlka ahipenakdr ipgivpmqip
1021 spevfeelik fsfhtnvled nigylrfdmf gdgelltqvs rllvehiwkk imhidamiid
1081 mrfniggpts sipilcsyff degppvlldk iysrpddsvs elwthaqvvg erygskksmv
1141 iltssvtagt aeeftyimkr lgralvigev tsggcqppqt yhvddtnlyl tiprarsvga
1201 sdgsswegvg vtphvvvpae ealarakeml qhnqlrvkrs pglqdhl     (SEQ ID NO: 2)
```

FIG. 10

```
   1 tgtccaccag ctgagaagga caagggcgga aggcagctgc acagagcagg gccacggcct
  61 tgcacacagt ccagggagct tttgtgcagg agccaggcct cccctgggt cccatgatg
 121 agagaatggg ttctgctcat gtccgtgctg ctctgtggcc tgctggccc cacacacctg
 181 ttccagccaa gcctggtgct ggacatggct aagtcctct tggataacta ctgcttcccg
 241 gagaacctgc tgggcatgca ggaagccatc cagcaggcca tcaagagcca tgagattctg
 301 agcatctcag acccgcagac gctggccagt gtgctgacag ccggggtgca gagctccctg
 361 aacgatcctc gcctggtcat ctcctatgag cccagcaccc cccagccctc cccacaagtc
 421 ccagcactca ccagcctctc agaagaggaa ctgcttgcct gggctgcaaag gggcctccgc
 481 catgaggttc tgagggtaa tgtgggctac ctgcgggtgg acagcgtccc gggccaggag
 541 gtgctgagca tgatggga gttcctggtg gccacgtgt ggggaatct catggcacc
 601 tccgccttag tgctggatct ccggcactgc acaggaggcc aggtctctgg cattcctac
 661 atcatctcct acctgcaccg aggaacacc atcctgcacg ttgcccagc ctactggt
 721 ccctccaaca ccaccacgga agggtcacca agccagccag agccagacca cgaggacatc
 781 gccgacaagg atgtggtggt ttaagcagat gcgcagggcc atcgtggtgg tgtctgactg
 841 gcgcacatcc ttcagcct gaggataggc gaggatctgact tcttcttcac ggtgccgtg
 901 gccctgaccc tccggaagct ggcagggcc agccagacgt gggagggcag cggggtgctg
 961 tccaggtccc tgggccct tggtggaggc cgagcaggcc ctgagaaaag gggaggcat cctcactctg
1021 ccctgtgtgg ggactccgg ttccaggag agtccactgc ctccagggag tcctgaagga ctactacacg
1081 tgcagcgcc ttccagggt gtgtgccac cctgctgcag cacttggcca gcatggactt ctactacacg
1141 ctggtggacc gtgtgccac cctgctgcag cacttggcca gcatggactt gcatggactt ctccacggtg
1201 gtctccgagg agatctggt caccaagctc caccaagctc tgcaggctgc gtctgaggat
1261 cccaggctcc tggtgcgagc catcggggcc aatgccgct cttcttggcc cgcgcccgac
1321 gctgcagccg aagactcacc agggtggcc acagaaactc ccaggttgc ctgaggacga ggctatccgg
1381 caagcactgg tggactctgt gttccaggtg tcggtgctgc caggcaatgt ctgaggacga ggctacctg
```

FIG. 10 (continued)

```
1441  cgcttcgata gtttgctga  cgcctccgtc  ctgggtgtgt  tggcccata   tgtcctgcgc
1501  caggtgtggg agccgctaca ggacacggag  caccctcatca tggacctgcg  ccacaaccct
1561  ggagggccat cctctgctgt gcccctgctc  ctgtcctact  tccagggccc  tgaggccggc
1621  cccgtgcacc tcttcaccac ctatgatcgc  cgcaccaaca  tcacgcagga  gcacttcagc
1681  cacatggagc tcccgggccc acgctacagc  acccaacgtg  gggtgtatct  gctcaccagc
1741  caccgcaccg ccacggccgc ggaggagttc  gccttcctta  tgcagtcgct  gggctgggcc
1801  acactggtag gtgagatcac cgcgggcaac  ctgctgcaca  cccgcacggt  gccgctgctg
1861  gacacacccg aaggcagcct cgcgcctcac  gtgccggtcc  tcacttcat   cgacaatcac
1921  ggcgaggcct ggctggggtgg tggagtggtg  cccgatgcca  tcgtgctggc  cgaggaggcc
1981  ctgacaaaag cccaggaagt gctggagttc  caccaaagcc  tggggcctt   ggtggagggc
2041  acagggcacc tgctggaggc ccactatgct  cggccagagg  tcgtggggca  gaccagtgcc
2101  ctcctgcggg ccaagctggc ccaaggcgcc  taccgcacag  ctgtggactt  ggagtctctg
2161  gcctctcagc tcacagcaga cctccaggag  gtgtctgggg  accacgctt   gctagtgttc
2221  cacagccctg gcgagctggt ggtagaggaa  gcaccccac   cagaggtgct  gcccgccag
2281  ccagaggagc tcacctacct tattgaggcc  ctgttcgagga cagtgaaggc  cgtggggcca
2341  ctgggctacc tcgttttga  cgccatggct  gaactggaga  cagtgaaggc  cgtggggcca
2401  cagcggtgtgc ggtcattgg  gcaacacagtg gtggacacgg  ctgcgctggt  gatcgacctg
2461  cgctacaacc ctggcagcta ctccacacct  atcccgctgc  tctgctccta  cttctttgag
2521  gcaggccccc gccagcacct gtattctgtc  tttgacaggg  ccacctcaaa  agtcacggag
2581  gtgtggacct tgccccaggt cgctacggct  cgctacggct  ccacctcaaa  cctctacatc
2641  ctgatgagcc acaccagtgg ctctgcgggg  gagccttg    cacacaccat  gcaggacctg
2701  cagggggcca cggtcattgg ggagccacg   gccgaggcg   cactctctgt  gggcatctac
2761  caggtgggca gcagcccctt atatgcatcc  atgccaccc   atggccat    gagtgccacc
2821  acaggcaagg cctgggacct ggctggtgtg  gagcccgaca  tcactgtgcc  catgagcgaa
```

FIG. 10 (continued)

```
2881  gcctttcca  tagcccagga  catagtggct  ctgcgtgcca  aggtgccac  ggtgctgcag
2941  acggccggga  agctggtggc  tgataactat  gcctctgccg  agctggggc  caagatggcc
3001  accaaactga  gcggtctgca  gagccgctac  tccaggtga  cctcagaagt  ggccctagcc
3061  gagatcctgg  gggctgacct  gcagatgctc  tccggagacc  cacacctgaa  ggcagcccat
3121  atccctgaga  atgccaagga  ccgcattcct  ggaattgtgc  ccatgcagat  cccttcccct
3181  gaagtatttg  aagagctgat  caagtttttcc  ttccacacta  acgtgcttga  ggacacatt
3241  ggctacttga  ggtttgacat  gtttggggac  ggtgagctgc  tcaccaggt  ctccaggctg
3301  ctggtggagc  acatctgaa  gaagatcatg  cacacggatg  ccatgatcat  cgacatgagg
3361  ttcaacatcg  gtggcccac  atcctccatt  ccccatcttgt  gctcctactt  ctttgatgaa
3421  ggccctccag  ttctgctgga  caagatctac  agccggcctg  atgactctgt  cagtgaactc
3481  tggacacacg  cccaggttgt  aggtgaacgc  tatggctcca  agaagagcat  ggtcattctg
3541  accagcagtg  tgacggccgg  caccgcgag  gagttcacct  atatcatgaa  gaggctgggc
3601  cgggccctgg  tcattgggga  ggtgaccagt  ggggctgcc  agccaccaca  gacctaccac
3661  gtggatgaca  ccaacctcta  cctcactatc  cccacggccc  gttctgtggg  ggcctcggat
3721  ggcagctcct  gggaagggt  ggggtgaca  aacccagcac  ccccatgtgg  ttgtccctgc  agaagaggct
3781  ctcgccaggg  ccaaggagat  gctccagcac  aaccagctga  gggtgaagcg  gagcccaggc
3841  ctgcaggacc  acctgtaggg  aaggggccca  taggcagagc  cccagggcag  acagaacctc
3901  tgggacacac  accaagggca  ctcctgcagg  tggcccggcc  tgaggttccc  aggagcagca
3961  aagggccctg  ctgagtctg  gttaggttac  agctggaggt  gtgtatatat  acacacacac
4021  acatgtatat  acacatatat  atgtgtatgt  atatatatat  ggctttccaa
4081  taaccacta  aatttaaca  aaggttcctt  ctaagtggta  gaacttgggg  tggtattttt
4141  accttcctc  ttcatactttt  gctcttttc  ttaaatactc  attaatgtgc  atatatcatt
4201  atttcagat  gcagctatca  ttattccaaa  atacaaaata  aagaagataa  aataaattat
4261  atacccgagc  cattaaaaa  aaaaaaaaa              (SEQ ID NO: 1)
```

No-Mild NPDR n=5 (from 4 Medalists)
PDR n=8 (from 5 Medalists)

FIG. 17

```
   1  tgggcggcgg  ctgaggcgcg  tgctctcgcg  tggtcgctgg  gtctgcgtct  tcccgagcca
  61  gtgtgctgag  ctctccgcgt  cgcctctgtc  gccgcgcct   ggcctaccgc  ggcactcccg
 121  gctgcacgct  ctgcttggcc  tcgccatgcc  ggtggacctc  agcaagtggt  ccggccctt
 181  gagcctgcaa  gaagtggacg  agcagccgca  gcaccgctg   catgtcacct  acgccggggc
 241  ggcggtggac  gagctgggca  aagtgctgac  gcccaccag   gttaagaata  gaccaccag
 301  catttcgtgg  gatgtcttg   attcaggga   gctctacacc  ttggtcctga  cagaccgga
 361  tgctcccagc  aggaaggatc  ccaaatacag  agaatggcat  catttcctgg  tggtcaacat
 421  gaagggcaat  gacatcagca  gtgcacagt   cctctccgat  tatgtgggct  cgggcctcc
 481  caagggcaca  ggcctccacc  gctatgtctg  gctggtttac  gagcaggaca  ggcgctaaa
 541  gtgtgacgag  cccatcctca  gcaaccgatc  tggagaccac  cgtggcaaat  tcaaggtggc
 601  gtccttccgt  aaaaagtatg  agctcagggc  cccggtggct  ggcacgtgtt  accaggccga
 661  gtgggatgac  tatgtgccca  aactgtacga  gcagctgtct  gggaagtagg  gggttagctt
 721  gggacctga   actgtcctgg  aggcccccaag ccattcagtg  cagttcagtg  ttgcatgtat
 781  aatagatttc  tcctcttcct  gcccccttg   gcatgggtga  gacctgacca  gtcagatggt
 841  agttgagggt  gactttttcct ctgcctggc   ctttataatt  ttactcactc  actctgattt
 901  atgttttgat  caaatttgaa  cttcattttg  ggggtatttt  tggtactgtg  atggggtcat
 961  caaattatta  atctgaaaat  agcaacccag  aatgtaaaaa  agaaaaaact  gggggaaaaa
1021  agaccaggtc  tacagtgata  gagcaaagca  tcaaagaatc  tttaagggag  gtttaaaaaa
1081  aaaaaaaaa   aaaaagattg  gttgcctctg  cctttgtgat  cctgagtcca  gaatggtaca
1141  caatgtgatt  ttatgtgtgat gtcactcacc  tagacaacca  gaggctggca  ttgaggctaa
1201  cctccaacac  agtgcatctc  agatgcctca  gtaggcatca  gtatgtcact  ctggtccctt
1261  taaagagcaa  tcctggaaga  agcaggaggg  agggtggctt  tgctgttgtt  gggacatggc
1321  aatctagacc  ggtagcagcg  ctcgctgaca  gcttgggagg  aaacctgaga  tctgtgtttt
1381  ttaaattgat  cgttcttcat  ggggtaaga   aaagctggtc  tggagttgct  gaatgttgca
```

FIG. 17 (continued)

```
1441 ttaattgtgc tgtttgcttg tagttgaata aaaatagaaa cctgaatgaa gaaaaaaaaa
1501 aaaaaaa   (SEQ ID NO: 3)

1 mpvdlskwsg plslqevdeq pqhplhvtya gaavdelgkv ltptqvknrp tsiswdglds
 61 gklytlvltd pdapsrkdpk yrewhhflvv nmkgndissg tvlsdyvgsg ppkgtglhry
121 vwlvyeqdrp lkcdepilsn rsgdhrgkfk vasfrkkyel rapvagtcyq aewddyvpkl
181 yeqlsgk   (SEQ ID NO: 4)
```

PREDICTING AND TREATING DIABETIC COMPLICATIONS

CROSS-REFERENCE TO RELATED APPLICATIONS

This application claims priority to U.S. Provisional application No. 61/420,686, filed Dec. 7, 2010, and PCT/US11/46672, filed Aug. 4, 2011, the contents of both of which are specifically incorporated by reference herein.

GOVERNMENT SUPPORT

This invention was made with Government support under grant number DK083957 awarded by the National Institutes of Health. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Aug. 13, 2013, is named JDP-145US02_SL.txt and is 20,595 bytes in size.

TECHNICAL FIELD

This invention relates to compositions and methods for diagnosing or predicting risk of diabetic retinopathy (DR) and/or diabetic nephropathy (DN), and to compositions and methods for treating DR and/or DN.

BACKGROUND

Common complications of diabetes (e.g., long-term diabetes) include DR and DN. Moreover, the majority of diabetics develop DR and/or DN.

SUMMARY

The present invention is based, at least in part, on the discovery of an association between certain biological factors and the incidence, risk, or development of a microvascular complication, e.g., DR (e.g., PDR) and/or DN. Accordingly, the present disclosure provides that certain of the factors disclosed herein can be used, e.g., as biomarkers to diagnose predict risk of developing a microvascular complication, e.g., DR and/or DN. The present disclosure also provides that certain of the factors disclosed herein can be used in the treatment or therapy of a microvascular complication, e.g., DR and/or DN.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 6 is a Table summarizing the clinical characteristics of the subjects disclosed in Examples 4-5.

FIG. 7 is a Table showing factors identified as being protective against PDR. (n=5 for no or mild to moderate DR. n=7 for PDR. Data was analyzed using the Kruskal Wallis test.)

FIG. 8 is a Table showing factors identified as being protective against DN. (n=9 for ACR less than 30 and with a histology class of 1. N=3 for ACR of greater than 30 and with a histology class greater than 1. Data was analyzed using the Kruskal Wallis test.)

FIG. 9 shows the amino acid sequence (SEQ ID NO: 2) of full length precursor of human RBP3 (SEQ ID NO: 2).

FIG. 10 shows the nucleotide sequence (SEQ ID NO: 1) of a cDNA encoding the full length precursor of human RBP3 (SEQ ID NO: 2).

FIG. 17 shows the nucleotide and amino acid sequence of human PEBP1 (SEQ ID NOs: 3 and 4, respectively).

DETAILED DESCRIPTION

Figure 1:
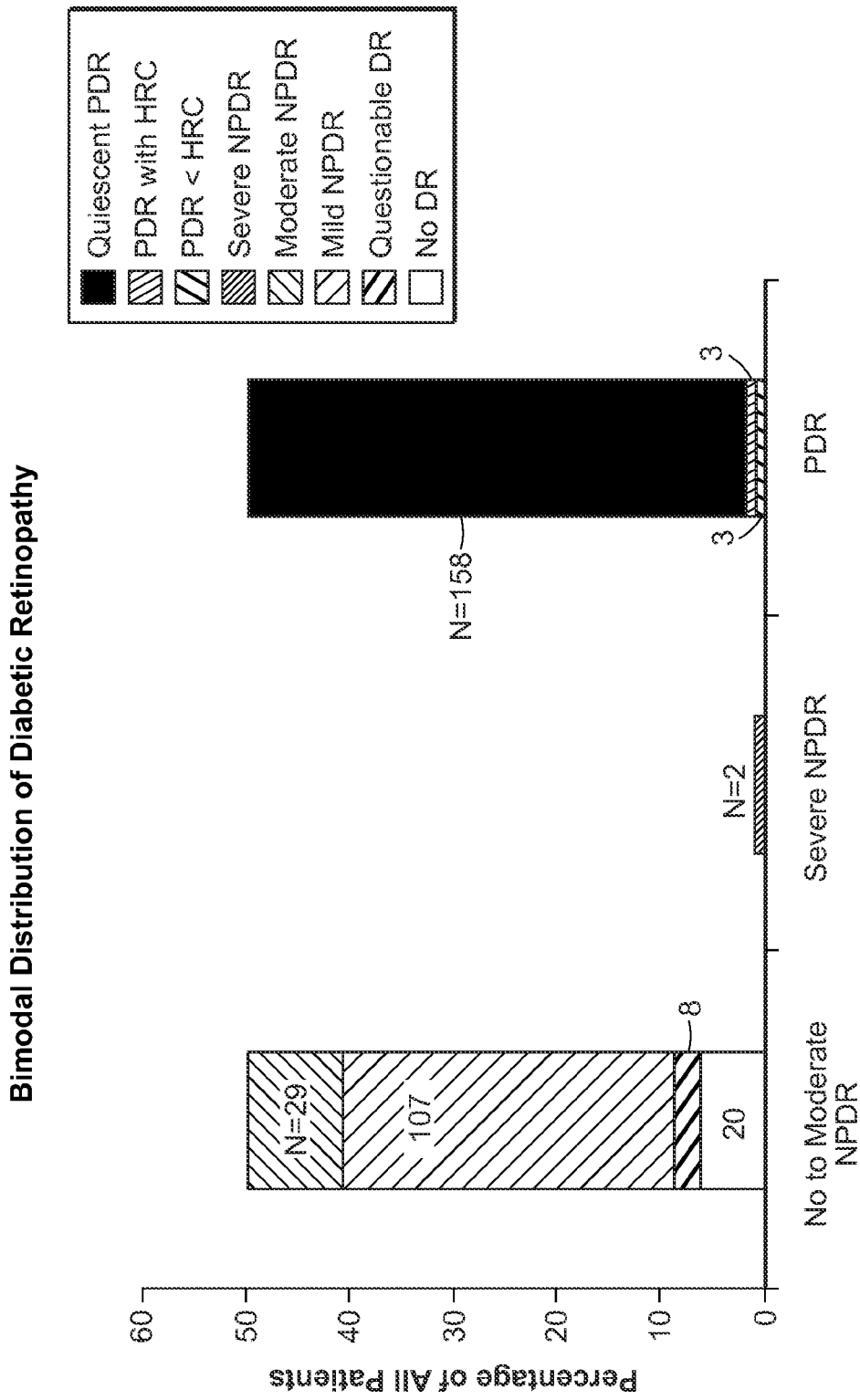
FIG. 1 is a bar graph showing the bimodal distribution of diabetic retinopathy in the Medalist subject population.

DR is damage that occurs to the retina of the eye in diabetics. Symptoms of DR range from blurred vision to loss of vision. Moreover, DR is a major cause of vision loss in developed countries. Understanding the causal role of vascular endothelial growth factor (VEGF) in the development of the proliferative DR (PDR) and vascular permeability has identified inhibitors of VEGF (e.g., AVASTIN and LUCENTIS) as effective treatments for diabetic neovascularization and macular edema. However, mechanisms by which hyperglycemia propagates the progression of DR are still not fully established. The only proven way to help prevent the initiation and progression of DR is good glycemic control. Several reasons may be responsible for the difficulty in identifying causal factors and effective treatments for the early stages of DR. These include challenges in obtaining retinal tissues in various stages of DR, lack of validated biomarkers and the absence of a salient rodent model. Recent therapeutic advances using inhibitors of VEGF for diabetic macular edema and neovascular lesions of DR are substantial. However, there remains a critical need to evaluate retinal tissue at all stages of DR to identify potential therapeutic targets and to validate potential markers of incidence and progression of DR in diabetic individuals.

DR is the result of microvascular retinal changes. The early stage of DR is referred to as non-proliferative diabetic retinopathy (NPDR), which is a stage during which blood vessels do not proliferate. NPDR can be separated out into mild NPDR, moderate NPDR, and severe NPDR. As DR progresses, blood vessels start to proliferate (i.e. grow) and new blood vessels form. This stage is referred to as proliferative diabetic neuropathy (PDR). These new blood vessels can bleed, cloud vision, and destroy the retina. Late stages may also involve retinal detachment and/or neovascular glaucoma. PDR can further be subdivided into two forms: (i) active PDR, wherein the blood vessels continue to develop and form; and (ii) quiescent PDR, which is described as PDR that is no longer active and is seen, e.g., in subjects having been treated with laser therapy.

Diabetic retinopathy severity grading is described in the following two references: 1: Grading diabetic retinopathy from stereoscopic color fundus photographs—an extension of the modified Airlie House classification. ETDRS report number 10. Early Treatment Diabetic Retinopathy Study Research Group. Ophthalmology. 1991 May; 98(5 Suppl): 786-806. PubMed PMID: 2062513; and 2: Fundus photographic risk factors for progression of diabetic retinopathy. ETDRS report number 12. Early Treatment Diabetic Retinopathy Study Research Group. Ophthalmology. 1991 May; 98(5 Suppl):823-33. PubMed PMID: 2062515. It is defined as follows:

1) Mild nonproliferative retinopathy (NPDR); At least one microaneurysm, and definition not met for moderate nonproliferative retinopathy, severe nonproliferative retinopathy, early proliferative retinopathy, or high-risk proliferative retinopathy (see below). ETDRS levels below 35. Level between 10 and 20 is very mild NPDR;
2) Moderate NPDR: Hemorrhages and/or microaneurysms≥standard photograph 2A*; and/or soft exudates, venous beading, or intraretinal microvascular abnormalities definitely present; and definition not met for severe nonproliferative retinopathy, early proliferative retinopathy, or high-risk proliferative retinopathy (see below). ETDRS levels 35, 43: moderate NPDR less than 4:2:1;
3) Severe NPDR: Soft exudates, venous beading, and intraretinal microvascular abnormalities all definitely present in at least two of fields four through seven; or two of the preceding three lesions present in at least two of fields four through seven and hemorrhages and microaneurysms present in these four fields, equaling or exceeding standard photo 2A in at least one of them; or intraretinal microvascular abnormalities present in each of fields four through seven and equaling or exceeding standard photograph 8A in at least two of them; and definition not met for early proliferative retinopathy or high-risk proliferative retinopathy (see below). ETDRS levels 53A-E: severe to very severe NPDR, 4:2:1 rule;
4) Early proliferative retinopathy (i.e., proliferative retinopathy without Diabetic Retinopathy Study high-risk characteristics): New vessels; and definition not met for high-risk proliferative retinopathy (see below); and
5) High-risk proliferative retinopathy (proliferative retinopathy with Diabetic Retinopathy Study high-risk characteristics): New vessels on or within one disc diameter of the optic disc (NVD)≥standard photograph 10A* (about one-quarter to one-third disc area), with or without vitreous or preretinal hemorrhage; or vitreous and/or preretinal hemorrhage accompanied by new vessels, either NVD<standard photograph 10A or new vessels elsewhere (NVE)≥one-quarter disc area. ETDRS levels 61, 65, 71, 75, 81, 85: PDR, high-risk PDR, very severe or advanced PDR.

Early Treatment Diabetic Retinopathy Study Research Group. Grading diabetic retinopathy from stereoscopic color fundus photographs—an extension of the modified Airlie House classification. ETDRS report number 10. Ophthalmology 1991; 98:786-806. Adapted from the Early Treatment Diabetic Retinopathy Study Research Group. Early Treatment Diabetic Retinopathy Study design and baseline patient characteristics. ETDRS report number 7. Ophthalmology 1991; 98:742.

DN is kidney disease or damage that occurs in diabetics. DN is a major cause of sickness and death in persons with diabetes. It is the leading cause of long-term kidney failure and end-stage kidney disease in the United States, and often leads to the need for dialysis or kidney transplantation.

As further described in the Examples, it has been shown herein that specific factors (e.g., proteins) are expressed at higher levels (e.g., at least 1.5 fold higher level) in type 1 diabetic individuals without a diabetic microvascular complication (DMC), such as diabetic retinopathy (DR) and diabetic nephropathy (DN), relative to type 1 diabetic individuals with DR or DN, respectively. Such factors are referred to as "protective factors." It has also been shown herein that specific factors (e.g., proteins) are expressed at lower levels in type 1 diabetic individuals without DN, relative to type 1 diabetic individuals with DN. Such factors are referred to herein as "risk factors."

Tables 2, 4 and FIG. 7 provide examples of factors that are expressed at higher levels in type 1 diabetic individuals without DR relative to those with DR. Table 6 provides factors with a statistically significant difference in expression (e.g., at least 1.5 fold) between type 1 diabetic individuals without DR and those with DR (see Examples 1 and 4), wherein individuals without DR have a higher level of the factors. These factors are DR protective factors.

TABLE 6

DR protective factors, exemplary accession numbers and fold increase in type 1 diabetes individuals without DR relative to those with DR

| | Name of DR protective factor | Accession Nos. | Fold increase |
|---|---|---|---|
| 1 | B3GNT1 N-acetyllactosaminide beta-1,3-Nacetylglucosaminyltransferase | IPI00009997 IPI00009997.1 | ∞ |

TABLE 6-continued

DR protective factors, exemplary accession numbers and fold increase in
type 1 diabetes individuals without DR relative to those with DR

| | Name of DR protective factor | Accession Nos. | Fold increase |
|---|---|---|---|
| 2 | LRP2 Low-density lipoprotein receptor-related protein 2 precursor | IPI00024292 IPI00024292.2 | ∞ |
| 3 | CD14 Monocyte differentiation antigen CD14 precursor | IPI00029260 IPI00029260.2 | ∞ |
| 4 | TNR Isoform 2 of Tenascin-R precursor | IPI00554760, IPI00554760.1, IPI00554760.2, IPI00554760.3 | ∞ |
| 5 | BTD Uncharacterized protein BTD (Fragment) | IPI00744685 IPI00744685.3 | ∞ |
| 6 | CHL1 Isoform 1 of Neural cell adhesion molecule L1-like protein precursor | IPI00783390 IPI00783390.2 | ∞ |
| 7 | IGLV1-40 V1-13 protein (Fragment) | IPI00789259 and EMBL CDS accession number AAF62890.1 | ∞ |
| 8 | COL18A1 Isoform 2 of Collagen alpha-1(XVIII) chain precursor | Protein COPa ID IPI00022822 | 16.80 |
| 9 | SEZ6 Isoform 3 of Seizure protein 6 homolog precursor | UniProt accession no. IPI00748395 | 10.73 |
| 10 | HSPG2 Basement membrane-specific heparan sulfate proteoglycan core protein precursor | EMBI-EBI accession no. IPI00024284 and IPI00024284.5 | 9.10 |
| 11 | APLP1 amyloid precursor-like protein 1 isoform 1 precursor | UniProt accession no. IPI00607600 and IPI00607600.3 | 9.10 |
| 12 | FCGBP IgGFc-binding protein precursor | IPI00242956 and NP_003881.2 | 7.55 |
| 13 | APLP2 Isoform 1 of Amyloid-like protein 2 precursor | EMBL-EBI accession no. IPI00031030 and IPI00031030.1 | 6.75 |
| 14 | TAGLN Transgelin | EMBL-EBI accession no. IPI00216138 and IPI00216138.6 | 4.20 |
| 15 | AGT Angiotensinogen precursor | EMBL-EBI accession no. IPI00032220 and IPI00032220.28 | 3.39 |
| 16 | C9 Complement component C9 precursor | EMBL-EBI IPI00022395 and IPI00022395.1 | 3.27 |
| 17 | Autotaxin isoform gamma | EMBI-EBL IPI00878576 and UniProt accession no. Q13822.3 | 2.84 |
| 18 | RBP3 Interphotoreceptor retinoid-binding protein precursor | IPI00022337 and IPI00022337.1 | 2.71 |
| 19 | Transthyretin | EMBL-EBI accession no. IPI00855916 and UniProt accession no. A6XGL1.1 | 2.68 |
| 20 | CST3; CST2 Cystatin-C precursor | EMBL-EBI accession no. IPI00032293 and IPI00032293.1 | 2.45 |
| 21 | A2M Alpha-2-macroglobulin precursor | EMBL-EBI accession no. IPI00478003 and IPI00478003.1 | 2.10 |
| 22 | CP Ceruloplasmin precursor | EMBL-EBI accession no. IPI00017601 and IPI00017601.1 | 1.58 |

Table 4 lists three factors that are expressed at lower levels in type 1 diabetic individuals without DR relative to those with DR. Table 7 provides factors with a statistically significant difference in expression (e.g., at least 1.5 fold) between type 1 diabetic individuals without DR and those with DR (see Examples 1 and 4), wherein individuals without DR have a lower level of the factors. These factors are DR risk factors. A fold decrease of "0" indicates essentially undetectable levels of the factor in a subject without DR (i.e., absence of the risk factor).

TABLE 7

DR protective factors, exemplary accession numbers and fold decrease in type 1 diabetes individuals without DR relative to those with DR

| | Name of DR risk factor | Accession Nos. | Fold decrease |
|---|---|---|---|
| 1 | CLEC3B Putative uncharacterized protein DKFZp686H17246 | EBML-EBI accession no. | 0.11 |
| 2 | AFM Afamin precursor | IPI00792115 and IPI00792115.1), IPI00019943 | 0 |
| 3 | CFD Complement factor D preproprotein | IPI00165972 | 0 |

Tables 3, 5 and FIG. 8 provide examples of factors that are expressed at higher levels in type 1 diabetic individuals without DN relative to those with DN. Table 8 provides factors with a statistically significant difference in expression (e.g., at least 1.5 fold) between type 1 diabetic individuals without DN and those with DN (see Examples 2 and 5), wherein individuals without DN have a higher level of the factors. These factors are DN protective factors.

TABLE 8

DN protective factors, exemplary accession numbers and fold increase in type 1 diabetes individuals without DN relative to those with DN

| | Name of DN protective factor | Accession Nos. | Fold increase |
|---|---|---|---|
| 1 | HDDC3 Isoform 1 of HD domain-containing protein 3 | IPI00789618 IPI00789618.3 | ∞ |
| 2 | IGJ immunoglobulin J chain | IPI00178926 IPI00178926.3 | 23.63 |
| 3 | Rheumatoid factor D5 light chain (Fragment) | IPI00816799 IPI00816799.1 | 11.00 |
| 4 | BPNT1 Isoform 2 of 3(2),5-bisphosphate nucleotidase 1 | IPI00410215 and UniProt O95861.85 | 8.00 |
| 5 | GNPDA1 Glucosamine-6-phosphate isomerase | IPI00009305 and UniProt P46926.107 | 6.60 |
| 6 | HPRT1 Uncharacterized protein HPRT1 | IPI00873466 and NP_003881.2 | 4.09 |
| 7 | GSTT1 Glutathione S-transferase theta 1 | IPI00893316 and UniProt C9JA47.9 | 3.48 |
| 8 | BHMT Betaine--homocysteine S-methyltransferase 1 | IPI00004101 and UniProt Q93088.2 | 3.22 |
| 9 | APOA1BP Isoform 2 of Apolipoprotein A-I-binding protein precursor | IPI00848298 and EMBL-EBI accession no. IPI00848298.1 | 2.69 |
| 10 | HPX Hemopexin precursor | IPI00022488 EMBL-EBI accession no. IPI00022488.1 | 2.44 |
| 11 | ALDOB Fructose-bisphosphate aldolase B | IPI00218407 and UniProt Q8NHT3.51 | 2.36 |
| 12 | AGMAT Agmatinase, mitochondrial precursor | IPI00305360 and UniProt Q9BSE5.88 | 2.35 |
| 13 | GATM Glycine amidinotransferase (L-arginine:glycine amidinotransferase) variant | IPI00792191 | 2.13 |
| 14 | PEBP1 Phosphatidylethanolamine-binding protein 1 | IPI00219446 and EMBL-EBI accession no. IPI00219446.5 | 2.11 |
| 15 | CS Citrate synthase, mitochondrial precursor | IPI00025366 IPI00025366.4 | 2.06 |

The bottom half of Table 5 provides examples of factors that are expressed at lower levels in type 1 diabetic individuals without DN relative to those with DN. Table 9 provides factors with a statistically significant difference in expression between type 1 diabetic individuals without DN and those with DN (see Example 5), wherein individuals without DN have a lower level of the factors. These factors are DN risk factors.

TABLE 9

DN risk factors, exemplary accession numbers and fold decrease in type 1 diabetes individuals without DN relative to those with DN

| | Name of DN risk factor | Accession Nos. | 1/Fold decrease | Fold decrease |
|---|---|---|---|---|
| 1 | TTLL3; ARPC4 Actin-related protein 2/3 complex subunit 4 | IPI00554811 IPI00554811.2 | 1/0.48 = 2.08 | 0.48 |
| 2 | CTNNA1 Isoform 1 of Catenin alpha-1 | IPI00215948 IPI00215948.4 | 1/0.42 = 2.38 | 0.42 |
| 3 | P4HB Protein disulfide-isomerase precursor | IPI00010796 IPI00010796.1 | 1/0.42 = 2.38 | 0.42 |
| 4 | RAB14 20 kDa protein | IPI00646415 and EMBL-EBI accession no. IPI00646415.1 | 1/0.35 = 2.86 | 0.35 |
| 5 | EEF1A1 Elongation factor 1-alpha | IPI00025447 and EMBL-EBI accession no. IPI00025447.8 | 1/0.32 = 3.13 | 0.32 |
| 6 | AP1B1 Isoform B of AP-1 complex subunit beta-1 | IPI00413947 and IPI00413947.2 | 1/0.31 = 3.23 | 0.31 |
| 7 | PDIA4 Protein disulfide-isomerase A4 precursor | IPI00009904 and IPI00009904.1 | 1/0.31 = 3.23 | 0.31 |
| 8 | CALR Calreticulin precursor | IPI00020599 and IPI00020599.1 | 1/0.28 = 3.57 | 0.28 |
| 9 | ACSL1 Isoform 2 of Long-chain-fatty-acid--CoA ligase 1 | IPI00401448 and IPI00401448.1 | 1/0.27 = 3.70 | 0.27 |
| 10 | PRKCSH protein kinase C substrate 80K-H isoform 2 | IPI00792916 and UniProt accession no. A8K318.8 | 1/0.23 = 4.35 | 0.23 |
| 11 | PDIA3 Protein disulfide-isomerase A3 precursor | IPI00025252 and IPI00025252.1 | 1/0.2 = 5.0 | 0.20 |
| 12 | CAP1 Adenylyl cyclase-associated protein 1 | IPI00008274 and UniProt accession no. Q01518.110 | 1/0.19 = 5.26 | 0.19 |
| 13 | KTN1 kinectin 1 isoform b | IPI00783726 UniProt accession no. Q17RZ5.32 | 1/0.17 = 5.88 | 0.17 |
| 14 | NDUFS2 NADH dehydrogenase [ubiquinone] iron-sulfur protein 2, mitochondrial precursor | IPI00025239 IPI00025239.2 | 1/0.14 = 7.14 | 0.14 |
| 15 | RAB6A Isoform 2 of Ras-related protein Rab-6A | IPI00217943 and UniProt accession no. P20340.131 | 1/0.12 = 8.33 | 0.12 |
| 16 | AP2A2 Adaptor-related protein complex 2, alpha 2 subunit variant (Fragment) | IPI00016621 and UniProt AP2A2.2 | ∞ | 0.00 |
| 17 | RPN1 Dolichyl-diphosphooligosaccharide--protein glycosyltransferase 67 kDa subunit precursor | IPI00025874 and IPI00025874.2 | ∞ | 0.00 |

In this table, Table 9, the fold changes were calculated from the following: the peptide numbers from individuals without DN were numerators, and the peptide numbers from individuals with DN were denominators. A fold number of "0.00" indicates that theses proteins were not detected in individuals without DN (therefore, decreased "infinitely").

The second to last column of the Table indicates the fold "decrease" as calculated by using 1 as numerators and using the numbers of the last column as denominators.

Methods of Diagnosis and Prognosis

The present disclosure provides, inter alia, methods and compositions for diagnosing and predicting risk of developing diabetic microvascular complications (DMCs), e.g., diabetic retinopathy (DR) and or diabetic nephropathy (DN), in a subject. The methods may also be used to determine the effectiveness of a therapy for a DMC or the prognosis of a subject. A method may comprise determining the level (e.g., protein or expression level) or activity of one or more protective or risk factors of a DMC, such as the factors described herein.

The methods include obtaining (or providing) a sample from a subject, e.g., a sample of an eye, such as vitreous, aqueous, or retinal tissue; tears; kidney tissue; plasma; or urine, and evaluating the presence and/or level of one or more biomarker described herein (e.g., in Table 2, 3, 4, 5, 6, 8, 7, 9 or FIG. 7 or 8) in the sample, and comparing the presence and/or level with one or more reference values, e.g., a control reference value that represents a normal level of the protein, e.g., a level in an unaffected subject, and/or a disease reference that represents a level of the proteins associated with DR or DN, e.g., a level in a subject having DR or DN or an increased (high) likelihood of developing DR or DN. In a preferred embodiment, the biomarker is a DR protective factor listed in Table 6, a DN protective factor listed in Table 8, a DR risk factor listed in Table 7, or a DN risk factor listed in Table 9.

Certain methods may comprise providing a sample from a subject (e.g., a subject having diabetes, e.g., type 1 diabetes), such as plasma, a kidney sample or an eye sample, e.g., a vitreous sample; determining the level of at least one protein (factor) listed in Table 2, 3, 4, 5, 6, 8, 7, 9 or FIG. 7 or 8, preferably a factor listed in Table 6, 8, 7, or 9, in the sample; and determining whether the at least one protein is present in the sample at levels at least 50%, 75% (i.e., 1½ fold), 100% (i.e., 2 fold), 2.5 fold, 3 fold, 4 fold, 5 fold, 10 fold, 15 fold or higher or lower than a control value (e.g., reference level), wherein the control value is, e.g., the level of the factor in a subject having type 1 diabetes for at least 10, 15, 20, 25, or more years and who has not developed a microvascular complication, and wherein (i) a level of one or more proteins of Table 6 that is lower by, e.g., at least 50%, 75% (i.e., 1½ fold), 100% (i.e., 2 fold), 2.5 fold, 3 fold, 4 fold, 5 fold, 10 fold, 15 fold or more relative to a control value, e.g., the level of the factor in a subject having type 1 diabetes for at least 10, 15, 20, 25, or more years and who has not developed DR, indicates that the subject has or is likely to develop DR (or a form thereof, e.g., an advanced form of NPDR, e.g., moderate or severe NPDR; or PDR, such as active or quiescent PDR; (ii) a level of one or more proteins of Table 8 that is lower by, e.g., at least 50%, 75% (i.e., 1½ fold), 100% (i.e., 2 fold), 2.5 fold, 3 fold, 4 fold, 5 fold, 10 fold, 15 fold, 20 fold or higher relative to a control value, e.g., the level of the factor in a subject having type 1 diabetes for at least 10, 15, 20, 25, or more years and who has not developed DN, indicates that the subject has or is likely to develop DN; and (iii) a level of one or more proteins of Table 7 or 9 that is higher by, e.g., at least 50%, 75% (i.e., 1½ fold), 100% (i.e., 2 fold), 2.5 fold, 3 fold, 4 fold, 5 fold, 10 fold, 15 fold or higher relative to a control value, e.g., the level of the factor in a subject having type 1 diabetes for at least 10, 15, 20, 25, or more years and who has not developed DR or DN, respectively, indicates that the subject has or is likely to develop DR or DN, respectively.

Certain methods may comprise providing a sample from a subject (e.g., a subject having diabetes, e.g., type 1 diabetes), such as plasma, a kidney sample or an eye sample, e.g., a vitreous sample; determining the level of at least one protein (factor) listed in Table 2, 3, 4, 5, 6, 8, 7, 9 or FIG. 7 or 8, preferably a factor listed in Table 6, 8, 7 or 9, in the sample; and determining whether the at least one protein is present in the sample at levels essentially identical (e.g., at most 10%, 20%, 30%, 40%, 50%, 60%, 70%, 80%, 90% or 100% higher or lower than) a control value (e.g., reference level), wherein the control value is, e.g., the level of the protein in a subject who has developed a microvascular complication (such as PDR, e.g., active or quiescent PDR; or NPDR, e.g., mild, moderate or severe NPDR), and wherein (i) a level of one or more proteins of Table 6 that is essentially identical to a control value, indicates that the subject has or is likely to develop DR (or a form thereof, e.g., advanced forms of NPDR, e.g., moderate or severe NPDR; or PDR, such as active or quiescent PDR); (ii) a level of one or more proteins of Table 8 that is essentially identical to a control value, e.g., the level of the factor in a subject having DN or a form thereof, indicates that the subject has or is likely to develop DN; and (iii) a level of one or more proteins of Table 7 or 9 that is essentially identical to a control value, e.g., the level of the factor in a subject having DR or DN, respectively, or a form thereof, indicates that the subject has or is likely to develop DR or DN, respectively.

In certain embodiments, the level of a DR protective factor in a subject is compared to both that in a subject who is protected, i.e., has not developed DR after at least 5, 10, 15, 20 or more years of disease, and that in a subject who has developed DR, e.g., severe NPDR or PDR, wherein a level of the DR protective factor in the subject that is significantly closer to that in a subject who is protected than to that in a subject having DR indicates that the subject is likely to be protected from developing DR, whereas a level of the DR protective factor in the subject that is significantly closer to that in a subject who has DR, e.g., severe NPDR or PDR, than to that in a subject that is protected indicates that the subject is likely to develop DR, e.g., severe NPDR or PDR.

In certain embodiments, the level of a risk factor in a subject is compared to both that in a subject who is protected, i.e., has not developed DR after at least 5, 10, 15, 20 or more years of disease, and that in a subject who has developed DR, e.g., severe NPDR or PDR, wherein a level of the risk factor in the subject that is significantly closer to that in a subject who is protected than to that in a subject having DR indicates that the subject is likely to be protected from developing DR, whereas a level of the risk factor in the subject that is significantly closer to that in a subject who has DR, e.g., severe NPDR or PDR, than to that in a subject that is protected indicates that the subject is likely to develop DR, e.g., severe NPDR or PDR.

In certain embodiments, the level of a DN protective factor in a subject is compared to both that of a subject who is protected, i.e., has not developed DR after at least 5, 10, 15, 20 or more years of disease, and that of a subject who has developed DN, wherein a level of the DN protective factor in the subject that is significantly closer to that in a subject who is protected than to that in a subject having DN indicates that the subject is likely to be protected from developing DN, whereas a level of the DN protective factor in the subject that is significantly closer to that in a subject who has DN, than to that of a subject that is protected indicates that the subject is likely to develop DN.

In certain embodiments, the level of a DN risk factor in a subject is compared to both that of a subject who is protected, i.e., has not developed DR after at least 5, 10, 15, 20 or more years of disease, and that of a subject who has developed DN, wherein a level of the DN risk factor in the subject that is significantly closer to that in a subject who is protected than to that in a subject having DN indicates that the subject is likely to be protected from developing DN, whereas a level of the DN risk factor in the subject that is significantly closer to that in a subject who has DN, than to that of a subject that is protected indicates that the subject is likely to develop DN.

A control or reference value may also be a statistically significant value obtained by, e.g., averaging the level of a particular factor present in more than 5, 10, 15, 20, 30, 40, 50, 100 or more individuals with particular characteristic, e.g., diabetes, but no DR or DN, or only mild forms thereof, such as mild NPDR.

A control or reference value is generally factor specific, and may be the value of the factor, e.g., a statistically significant value of the factor, in (i) one or more subjects that are protected from a microvascular complication or (ii) one or more subjects that have a microvascular complication. These two types of control or reference values may be referred to "protected control value" (for the value found in protected subjects) and "disease control value" (for the value found in diseases subjects). A reference value may depend on the stage of the microvascular complication. For example, an "RBP3 control value" or "RBP3 reference value" is a control or reference value of RBP3, e.g., the value of RBP3 in one or more subjects that are protected (e.g., a subject having diabetes for over 5, 10, 15, 20, 25, 30, 35, 40, 45 or 50 years and not having developed DR; an "RBP3 protected control value") or the value of RBP3 in one or more subjects that are not protected and have or are likely to develop DR (an "RBP3 disease control value," such as "RBP3 severe NPDR control value" or "RBP3 PDR control value").

In one embodiment, the level of RBP3 is measured in a subject, e.g., a subject with type 1 or 2 diabetes, to determine the likelihood of the subject to develop a DR complication, e.g., severe NPDR and PDR. The level of RBP3 may be measured, e.g., in the vitreous, retina, plasma or urine of the subject. The level of RBP3 may also be predictive of the effectiveness of a treatment or determining the prognosis of a DR complication. A method may comprise obtaining a sample from a subject and determining the level of RBP3 in the sample. The presence of a lower level (e.g., 1.5 or 2 fold lower) of RBP3 relative to a reference value, e.g., the level of RBP3 in type 1 diabetes subjects who have not developed DR after at least 5, 10, 15, 20 or more years of disease is indicative of the likelihood of the subject to have or to develop an advanced stage of NPDR, e.g., severe, NPDR or PDR, or a poor prognostic of the DR. A method may also comprise comparing the level of RBP3 in a subject to a reference level that is the level of RBP3 (e.g., in the vitreous, retina, plasma or urine) that is present in a subject having NPDR, e.g., mild, moderate or severe NPDR, or having PDR. A subject that is found to have a similar level of RBP3 protein relative to that in a subject having severe NPDR or PDR is likely to develop a DR complication, e.g., severe NPDR or PDR. In certain embodiments, the level of RBP3 in a subject is compared to both that in a subject who is protected, i.e., has not developed DR after at least 5, 10, 15, 20 or more years of disease, and that in a subject who has developed DR, e.g., severe NPDR or PDR, wherein a level of RBP3 in the subject that is significantly closer to that in a subject who is protected than to that in a subject having DR indicates that the subject is likely to be protected from developing DR, whereas a level of RBP3 in the subject that is significantly closer to that in a subject who has DR, e.g., severe NPDR or PDR, than to that in a subject that is protected indicates that the subject is likely to develop DR, e.g., severe NPDR or PDR.

In one embodiment, the level of PEBP1 is measured in a subject, e.g., a subject with type 1 or 2 diabetes, to determine the likelihood of the subject from developing a kidney complication, e.g., DN. The level of PEBP1 may also be predictive of the effectiveness of a treatment or determining the prognosis of a kidney complication. A method may comprise obtaining a kidney sample (e.g., sample of glomeruli) from a subject and determining the level of PEBP1 in the sample. The presence of a lower level (e.g., 1.5 or 2 fold) of PEBP1 relative to a reference value, e.g., the level of PEBP1 in type 1 diabetes subjects who have not developed DN after at least 5, 10, 15, 20 or more years of disease is indicative of the likelihood of the subject to have or to develop DN or a poor prognostic of DN. A method may also comprise comparing the level of PEBP1 in a subject to a reference level that is the level of PEBP1 that is present in a subject having DN. A subject that is found to have a similar level of PEBP1 protein relative to that of a subject having DN is likely to develop a kidney complication, e.g., DN. In certain embodiments, the level of PEBP1 in a subject is compared to both that of a subject who is protected, i.e., has not developed DR after at least 5, 10, 15, 20 or more years of disease, and that of a subject who has developed DN, wherein a level of PEBP1 in the subject that is significantly closer to that in a subject who is protected than to that in a subject having DN indicates that the subject is likely to be protected from developing DN, whereas a level of RBP3 in the subject that is significantly closer to that in a subject who has DN, than to that of a subject that is protected indicates that the subject is likely to develop DN.

In certain embodiments, an increased level of a protective factor or reduced level of a risk factor is predictive of protection from a particular (or single) microvascular complication, such as DR, e.g., PDR, or DN. In certain embodiments, an increased level of a protective factor or reduced level of a risk factor is predictive of protection from more than one microvascular complication, e.g., both DR and DN. For example, an increased level of GPX3, e.g., in plasma indicates a reduced risk of a subject to develop DR or DN.

In certain embodiments, a method comprises determining the protein level of at least 2, 3, 4, 5, 6, 7, 8, 9, 10, 11, 12, 13, 14, 15, 16, 17, 18, 19, 20, 25, 30 or more protective or risk factors of Tables 6, 8, 7 or 9. In certain embodiments, a method comprises determining the protein level of 1-58, 1-50, 1-45, 1-40, 1-35, 1-30, 1-25, 1-20, 1-15, 1-10, 1-5, 1-4, 1-3 or 1-2 protective or risk factors set forth in Tables 6, 8, 7 or 9. Preferred combinations of protective factors to be measured for determining the likelihood of a subject to have or to develop DR include RBP3 and or more other factors in Table 6. In certain embodiments, the level of PEDF is also measured, wherein an increased level of PEDF is protective against DR, e.g., PDR. In certain embodiments, the level of PEBP1 and that of at least one other factor, e.g., in Table 8 or 9 is measured.

The level or concentration of protective or risk factors may be determined in a tissue sample, such as a kidney sample (e.g., renal glomeruli sample), eye vitreous or retina, or bodily fluid sample, e.g., urine, blood, plasma, or intraocular fluid. Protective or risk factors for DR may be measured in an eye sample, e.g., a sample of the vitreous, retina or intraocular fluid, of a subject. Protective or risk factors for DN may be measured in a kidney sample, e.g., a renal glomerulus sample.

A "level of a factor" refers to the quantity or concentration of the protein or RNA (e.g., RNA) of the factor, and may also refer to the measurement of any other factor that results in the determination of the level of the factor (e.g., the measurement of the level of a metabolite of an enzyme may be a measurement of the level of the enzyme). Similarly, measurements of upstream products may also be measurements of the level of a factor.

In certain embodiments, the level or concentration of one or more factor is measured in the blood or plasma of a subject. For example, the level of GPX3 may be measured in plasma, wherein an increased (or higher) level of GPX3 in plasma of a first subject relative to that in a second subject indicates that the first subject is less likely than the second subject to develop a kidney problem, such as DN; whereas reduced levels of GPX3 in plasma of a first subject relative to that in a second subject indicates that the first subject is more likely than the second subject to develop a kidney problem, e.g., DN (see Example 3). The level of RBP3 may be measured in plasma, wherein an increased (or higher) level of RBP3 in plasma of a first subject relative to that in a second subject indicates that the first subject is less likely than the second subject to develop a kidney problem, such as DN; whereas reduced levels of RBP3 in plasma of a first subject relative to that in a second subject indicates that the first subject is more likely than the second subject to develop a DR, e.g., PDR (see Example 6). In certain embodiments, the plasma level or concentration of both GPX3 and RBP3 is measured in a subject, e.g., to determine the likelihood of a subject to develop DR and/or DN. Any of the other factors described herein may also be measured in plasma, particularly if the factor is a soluble factor, e.g., a factor that is produced in a secreted form from a cell or a factor, e.g., a membrane bound factor, that is shed by a cell.

A higher level of a protective factor, e.g., RBP3, or reduced level of a risk factor can also be used as a measure of the success of a treatment. For example, a subject having type 1 diabetes who is responding positively to a diabetic treatment may have a higher level of a protective factor and/or a lower level of a risk factor relative to a subject having type 1 diabetes who is not responding to a treatment or to the value of the factor at the beginning of the treatment of the subject. Thus, an increase in the level of a protective factor and/or a decrease in the level of a risk factor in a subject with type 1 diabetes who is being treated indicates that the subject responds positively to the treatment.

The presence and/or level of a protein can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of a biomarker listed herein (e.g., in Table 2, 3, 4, 5, 6, 8, 7, 9 or FIG. 7 or 8, preferably Table 6, 8 or 9).

In some embodiments, once it has been determined that a person has DR or DN, or has an increased risk of developing DR or DN, then a treatment, e.g., as known in the art or as described herein, can be administered.

The compositions disclosed herein can include agents that detect or bind (e.g., that detect or bind specifically) to a biomarker described herein (e.g., in Table 2, 3, 4, 5, 6, 8, 7, 9 or FIG. 7 or 8, preferably Table 6, 8, 7 or 9). Such agents can include, but are not limited to, for example, antibodies, antibody fragments, and peptides. In some instances, the compositions can be in the form of a kit. Such kits can include one or more agents that can detect or bind (e.g., that detect or bind specifically) to one or more biomarkers described herein (e.g., one or more of the biomarkers disclosed in Table 2, 3, 4, 5, 6, 8, 7, 9 or FIG. 7 or 8, preferably Table 6, 8, 7 or 9) and instructions for use.

In certain embodiments, a method comprises determining the level of a protective or risk factor in a subject. The measurement may be performed in the subject, e.g., by imaging, or on a sample obtained from a subject. If the level of the factor is determined in a sample of a subject, a method may comprise first obtaining a sample from a subject, e.g., by using a needle or other apparatus to aspirate a sample. A sample may then be sent to a laboratory for determining the level of the factor, following the doctor's instructions. If the measuring is performed in the subject, the subject may be sent to a particular department in the hospital where they handle such matters, following the doctor's instructions. The level of the factor, as determined in the laboratory or hospital is then sent back to the doctor who had ordered the measurement, or entered into a computer or data system that is accessible to the doctor. The doctor may then compare the value(s) received to reference values, which may, e.g., be present in a computer. For example, the doctor may enter the values into a computer, and the computer performs the comparison with one or more control values. The computer may also provide the conclusion regarding the likelihood of development of a microvascular complication by the subject. The doctor may then discuss the results with the subject, and choose a path forward, e.g., an appropriate treatment; the decision to re-evaluate the level of one or more factors at a later time; or to evaluate other criteria of the subjects, e.g., the presence or absence of certain symptoms.

Methods of Treatment

As used herein, "treatment" means any manner in which one or more of the symptoms of DR and/or DN are ameliorated or otherwise beneficially altered. As used herein, amelioration of the symptoms of the disorder refers to any lessening, whether permanent or temporary, lasting or transient that can be attributed to or associated with treatment by the compositions and methods of the present invention. For example, with DR, treatment can include lessening of any symptom associated with DR, including, but not limited to, blurred or distorted vision or difficulty reading, floaters, reduced vision, vision loss, pain, and/or bleeding in the eye. Similarly, with DN, treatment can include lessening of any symptom associated with DN, including, but not limited to, changes in appetite, change in sleep, protein in serum, weakness, and/or nausea.

In some embodiments, the present disclosure provides methods for treating a microvascular complication, e.g., DR and/or DN, in a subject (e.g., a subject with diabetes (e.g., type 1 and/or type 2 diabetes) by administering to the subject a therapeutically effective amount of one or more (e.g., 1, 2, 3, 4, 5, 6, 7, 8, 9, 10, 11, 12, 13, 14, 15, 16, 17, 18, 19, 20, or more, including all) agents that increase the level or activity of one or more of the DR protective factors disclosed in Table 6 for treating or preventing DR or increase the level or activity of one or more of the DN protective factors disclosed in Table 8 for treating or preventing DN. In certain embodiments, a treatment comprises administering to a subject in need thereof a therapeutically effective amount of an agent that reduces the level or activity of a DR or DN risk factor of Table 7 or 9, respectively. An agent may increase the level or activity of a protective factor or decrease the level or activity of a risk factor by at least 50%, 100% (1 fold), 1½ fold, 2 fold, 3 fold, 4 fold, 5 fold, 10 fold, 15 fold, 20 fold or more. In certain embodiments, a therapeutic method comprises bringing the level or activity of a protective or risk factor essentially to its level or activity in a subject that is protected from the development of a microvascular complication. "Essentially within its level," refers to within less than 5%, 10%, 20%, 30%, 40%, 50%, 60%, 70%, 80%, 90% or 100% of the control value. How close the level or activity can be brought to a control value depends on the particular factor, in particular on how different the level of the factor is in a protected subject versus a diseased subject.

An agent that increases the level or activity of a protective factor may be a small molecule, a protein comprising the protective factor or a biologically active variant (e.g., fragment) thereof, or a nucleic acid encoding a protein comprising the protective factor or a biologically active variant (e.g., fragment) thereof. An agent that reduces the level or activity of a risk factor may be a small molecule, an RNAi inhibitory molecule (e.g., an siRNA or hsRNA molecule), an antisense molecule, a ribozyme, or an aptamer.

Accordingly, the present disclosure includes treatments comprising administering one or more proteins, or nucleic acid(s) encoding the one or more proteins, consisting of, consisting essentially of, or comprising the amino acid sequences, or variants thereof, that are associated with any one or more of the accession numbers of the factors disclosed in Table 6 and/or 8. For example, useful amino acid sequences can have 50%, 60%, 70%, 80%, 85%, 90%, 95%, 98%, 99%, or 100% sequence identity to any one or more of the accession numbers disclosed in Table 6 and/or 8, provided that they retain the necessary biological activity of the factor for its protective characteristics.

The present disclosure also contemplates use of nucleic acid sequences that encode amino acid sequences consisting of, consisting essentially of, or comprising the amino acid sequences associated with any one or more of the accession numbers disclosed in Table 6 and/or 8 or variants thereof. For example, useful nucleic acid sequences can encode an amino acid sequence with 50%, 60%, 70%, 80%, 85%, 90%, 95%, 98%, 99%, or 100% sequence identity to any one or more of the accession numbers disclosed in Table 6 and/or 8.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

Useful proteins can also comprise amino acid sequences consisting of, consisting essentially of, or comprising the amino acid sequences associated with any one or more of the accession numbers disclosed in Table 6 and/or 8 with one or more (e.g., 1, 2, 3, 4, 5, 6, 7, 8, 9, 10, 20, 30, 40, 50, 60, 70, 80, 90, 100, or any range between any of the afore listed integers, or more than 100) amino acid additions, deletions or substitutions, e.g., conservative amino acid substitutions, provided that the protein retains the necessary biological activity of the factor for its protective characteristics. Conservative amino acid substitutions are known in the art.

In some embodiments, useful proteins can include modified proteins that possess at least a portion of the activity (e.g., biological activity) of the unmodified proteins. For example, modified proteins can retain 50%, 60%, 70%, 80%, 85%, 90%, 95%, 98%, 99%, or 100% of the activity (e.g., biological activity) of the unmodified proteins, e.g., the unmodified version of the amino acid sequences associated with any one or more of the accession numbers disclosed in Table 6 and/or 8.

In some embodiments, useful proteins include proteins that comprise a biologically active fragment of any one or more of the factors disclosed in Table 6 and/or 8.

In some embodiments, treatment of DR or prevention of DR can include administering one or more of the following proteins or biologically active variants thereof or nucleic acid encoding such to a subject in need of such treatment or prevention: B3GNT1 N-acetyllactosaminide beta-1,3-N-acetyl-glucosaminyltransferase (e.g, IPI00009997 and IPI00009997.1), LRP2 Low-density lipoprotein receptor-related protein 2 precursor (e.g., IPI00024292 and IPI00024292.2), CD14 Monocyte differentiation antigen CD14 precursor (e.g., IPI00029260 and IPI00029260.2), TNR Isoform 2 of Tenascin-R precursor (e.g., IPI00554760, IPI00554760.1, IPI00554760.2, and IPI00554760.3), BTD Uncharacterized protein BTD (Fragment) (e.g., IPI00744685 and IPI00744685.3), CHL1 Isoform 1 of Neural cell adhesion molecule L1-like protein precursor (e.g., IPI00783390 and IPI00783390.2), IGLV1-40 V1-13 protein (Fragment) (e.g., IPI00789259 and EMBL CDS accession number AAF62890.1), COL18A1 Isoform 2 of Collagen alpha-1 (XVIII) chain precursor (e.g., Protein COPa ID IPI00022822), SEZ6 Isoform 3 of Seizure protein 6 homolog precursor (e.g., UniProt accession no. IPI00748395), HSPG2 Basement membrane-specific heparan sulfate proteoglycan core protein precursor (e.g., EMBI-EBI accession no. IPI00024284 and IPI00024284.5), APLP1 amyloid precursor-like protein 1 isoform 1 precursor (e.g., UniProt accession no. IPI00607600 and IPI00607600.3), FCGBP IgGFc-binding protein precursor (e.g., IPI00242956 and NP_003881.2), APLP2 Isoform 1 of Amyloid-like protein 2 precursor (e.g., EMBL-EBI accession no. IPI00031030 and IPI00031030.1), TAGLN Transgelin (e.g., EMBL-EBI accession no. IPI00216138 and IPI00216138.6), AGT Angiotensinogen precursor (e.g., EMBL-EBI accession no. IPI00032220 and IPI00032220.28), C9 Complement component C9 precursor (e.g., EMBL-EBI IPI00022395 and IPI00022395.1),—Autotaxin isoform gamma (e.g., EMBI-EBL IPI00878576 and UniProt accession no. Q13822.3), RBP3 Interphotoreceptor retinoid-binding protein precursor (e.g., IPI00022337 and IPI00022337.1),—Transthyretin (EMBL-EBI accession no. IPI00855916 and UniProt accession no. A6XGL1.1), CST3; CST2 Cystatin-C precursor (e.g., EMBL-EBI accession no. IPI00032293 and IPI00032293.1), A2M Alpha-2-macroglobulin precursor (e.g., EMBL-EBI accession no. IPI00478003 and IPI00478003.1), and CP Ceruloplasmin precursor (e.g., EMBL-EBI accession no. IPI00017601 and IPI00017601.1).

In some embodiments, treatment of DN or prevention of DN can include administering one or more of the following proteins or biologically active variants thereof or nucleic acid encoding such to a subject in need of such treatment or prevention: IPI00789618 (e.g., HDDC3 Isoform 1 of HD domain-containing protein 3, IPI00789618.3), IPI00178926 (IGJ immunoglobulin J chain and IPI00178926.3), IPI00816799 (Rheumatoid factor D5 light chain (Fragment) and IPI00816799.1), IPI00410215 (BPNT1 Isoform 2 of 3(2), 5-bisphosphate nucleotidase 1 and UniProt O95861.85), IPI00009305 (GNPDA1 Glucosamine-6-phosphate isomerase and UniProt P46926.107), IPI00873466 (HPRT1 Uncharacterized protein HPRT1 and NP_003881.2), IPI00893316 (GSTT1 Glutathione S-transferase theta 1 and UniProt C9JA47.9), IPI00004101 (BHMT Betaine—homocysteine 5-methyltransferase 1 and UniProt Q93088.2), IPI00848298 (APOA1BP Isoform 2 of Apolipoprotein A-I-binding protein precursor and EMBL-EBI accession no. IPI00848298.1), IPI00022488 (HPX Hemopexin precursor and EMBL-EBI accession no. IPI00022488.1), IPI00218407 (ALDOB Fructose-bisphosphate aldolase B and UniProt Q8NHT3.51), IPI00305360 (AGMAT Agmatinase, mitochondrial precursor and UniProt Q9BSE5.88), IPI00792191 (GATM Glycine amidinotransferase (L-arginine:glycine amidinotransferase) variant), IPI00219446 (PEBP1 Phosphatidylethanolamine-binding protein 1 and EMBL-EBI accession no. IPI00219446.5), and IPI00025366 (CS Citrate synthase, mitochondrial precursor and IPI00025366.4).

In certain embodiments, treatment of DR or prevention of DR can include administering an agent that inhibits or reduces the expression or activity of one or more of: CLEC3B Putative uncharacterized protein DKFZp686H17246 (e.g., EBML-EBI accession no. IPI00792115 and IPI00792115.1), AFM Afamin precursor (e.g., IPI00019943), CFD Complement factor D preproprotein (e.g., IPI00165972), and PTGDS in a subject.

In some embodiments, treatment of DN or prevention of DN can include administering an agent that inhibits or reduces the expression or activity of one or more of: IPI00554811 (TTLL3; ARPC4 Actin-related protein 2/3 complex subunit 4 and IPI00554811.2), IPI00215948 (CTNNA1 Isoform 1 of Catenin alpha-1 and IPI00215948.4), IPI00010796 (P4HB Protein disulfide-isomerase precursor and IPI00010796.1), IPI00646415 (RAB14 20 kDa protein and EMBL-EBI accession no. IPI00646415.1), IPI00025447 (EEF1A1 Elongation factor 1-alpha and EMBL-EBI accession no. IPI00025447.8), IPI00413947 (AP1B1 Isoform B of AP-1 complex subunit beta-1 and IPI00413947.2), IPI00009904 (PDIA4 Protein disulfide-isomerase A4 precursor and IPI00009904.1), IPI00020599 (CALR Calreticulin precursor and IPI00020599.1), IPI00401448 (ACSL1 Isoform 2 of Long-chain-fatty-acid—CoA ligase 1 and IPI00401448.1), IPI00792916 (PRKCSH protein kinase C substrate 80K-H isoform 2 and UniProt accession no. A8K318.8), IPI00025252 (PDIA3 Protein disulfide-isomerase A3 precursor and IPI00025252.1), IPI00008274 (CAP1 Adenylyl cyclase-associated protein 1 and UniProt accession no. Q01518.110), IPI00783726 (KTN1 kinectin 1 isoform b and UniProt accession no. Q17RZ5.32), IPI00025239 (NDUFS2 NADH dehydrogenase [ubiquinone] iron-sulfur protein 2, mitochondrial precursor and IPI00025239.2), IPI00217943 (RAB6A Isoform 2 of Rasrelated protein Rab-6A and UniProt accession no. P20340.131), IPI00016621 (AP2A2 Adaptor-related protein complex 2, alpha 2 subunit variant (Fragment) and UniProt AP2A2.2), and IPI00025874 (RPN1 Dolichyl-diphosphooligosaccharide—protein glycosyltransferase 67 kDa subunit pre and IPI00025874.2) in a subject.

In certain embodiments, RBP3, e.g., human RBP3, or a biologically active variant thereof is administered to a subject having or likely to develop DR, e.g., PDR, or to protect the cells of a subject from high glucose exposure. "RBP3" refers to "retinol binding protein 3, interstitial," and is also referred to as interphotoreceptor retinoid-binding protein, IRBP, D10S64, D10S65, D10S66, and RBPI. As indicated in the NCBI Gene database, RBP3 is a large glycoprotein known to bind retinoids and found primarily in the interphotoreceptor matrix of the retina between the retinal pigment epithelium and the photoreceptor cells. It is thought to transport retinoids between the retinal pigment epithelium and the photoreceptors, a critical role in the visual process. The amino acid sequence of human RBP3 can be divided into four contiguous homology domains with 33-38% identity. The precursor of the human RBP3 protein is 1247 aa long and has the amino acid sequence set forth in GenBank Accession No. NP_002891. The nucleotide and amino acid sequences of human RBP3 are set forth as SEQ ID NOs: 1 and 2, respectively, and shown in FIG. 9. The signal peptide of human RBP3 corresponds to amino acids 1-17. The mature protein consists of amino acids 18-1247. The protein comprises four domains referred to as Peptidase_S41_IRBP regions. These domains are located at amino acids 27 to 318 of SEQ ID NO: 2, amino acids 329 to 626 of SEQ ID NO: 2, amino acids 639 to 931 of SEQ ID NO: 2, and amino acids 940 to 1226 of SEQ ID NO: 2. The xenopus RBP3 has been crystallized and its structure solved (Ghosh D et al, Mol Vis. 2007 Dec. 13; 13:2275-81), and from sequence homology some regions can be predicted. The authors conclude that the data may indicate that the retinol-binding site is restricted to one of the four modules, or to an intramodule site defined by multiple modules, consistent with the notion that not all four modules are functionally equivalent as the homology modeling results indicated.

A homozygous missense mutation (pAsp1080Asn) in human RBP3 has been reported to be associated with retinitis pigmentosa (den Hollander et al. Invest. Ophthalmol. Vis. Sci. April 2009 vol. 50 no. 4 1864-187), and the authors predict that this residue participates in the retinol binding domain of the human RBP3 protein.

The nucleotide sequence of a cDNA encoding full length human RBP3 precursor (SEQ ID NO: 1) consists of 4289 nucleotides, wherein nucleotides 115 to 3858 encode SEQ ID NO: 2. The signal peptide is encoded by nucleotides 115 to 165, and the mature protein is encoded by nucleotides 166 to 3855 of SEQ ID NO: 1.

Biologically active variants of the full length human RBP3 protein (having SEQ ID NO: 2 or the mature form thereof) that may be used in therapeutic methods for treating DR include those comprising an amino acid sequence that comprises fewer amino acids than SEQ ID NO: 2 or the mature form thereof, and contains, e.g., at most 5, 10, 20, 30, 50, 100, 200, 300, 400, 500, 600, 700, 800, 900, 1000 or more, fewer amino acids. A biologically active fragment of human RBP3 may comprise 1, 2, 3 or all 4 homology domains. Other biologically active fragments of human RBP3 include those that retain the ability to bind to retinol or other lipid, e.g., they comprise Asp1080.

Biologically active variants of human RBP3 also include full length immature and mature forms of human RBP3 or fragments thereof that comprise an amino acid sequence that differs from SEQ ID NO: 2 or fragment thereof in at most 1, 2, 3, 4, 5, 10, 15, 20, 25, 30, 35, 40, 45, 50 or 100 amino acid deletions, additions or substitutions, such as conservative amino acid substitutions. Biologically active variants of a human RBP3 protein may also include variants that are at least 70%, 80%, 85%, 90%, 95%, 97%, 98% or 99% identical to the full length mature or precursor human RBP3 protein or a fragment thereof.

Biologically active variants of human PEBP1 also include full length immature and mature forms of human PEBP1 or fragments thereof that comprise an amino acid sequence that differs from the naturally occurring sequence (e.g., SEQ ID NO: 4; GenBank Accession No. NP_002558; encoded by a nucleotide sequence having GenBank Accession No. NM_002567 and set forth herein as SEQ ID NO: 3; FIG. 17) or fragment thereof in at most 1, 2, 3, 4, 5, 10, 15, 20, 25, 30, 35, 40, 45, 50 or 100 amino acid deletions, additions or substitutions, such as conservative amino acid substitutions. Biologically active variants of a human PEBP1 protein may also include variants that are at least 70%, 80%, 85%, 90%, 95%, 97%, 98% or 99% identical to the full length mature or precursor human PEBP1 protein or a fragment thereof.

The present disclosure also includes fusion proteins comprising any one or more amino acid sequence disclosed in Table 6 and/or 8 in combination with a moiety that increases the stability of the fusion protein in vivo (e.g., polyethelene glycol (PEG)) and/or that increases transport of the fusion protein to the therapeutic target (e.g., the eye and/or the kidney).

As further described herein, protein may be administered systemically or locally. For example, a protein for treating or preventing DR, e.g., human RBP3 or a biologically active variant thereof, may be administered directly into the eye, e.g., in the vitreous, e.g., by injection. For example, a protein may be injected into the eye using the same or a similar methodology as that used for administered LUCENTIS or AVASTIN to the eye of a subject. An agent for treating or preventing DR may also be administered to the eye in the form of drops or a periocular injection (peribulbar or subconjunctival).

In certain embodiments, a protein for treating DR, e.g., human RBP3 or a biologically active variant thereof, may be administered with another agent for treating or preventing DR, such as LUCENTIS or AVASTIN. Two or more pharmaceutical agents may be administered simultaneously or sequentially. They may be present in one pharmaceutical composition or more than one pharmaceutical composition.

Systemic administration is also expected to be functional, e.g., for treating DR, as the retinal blood barrier is leaky in diabetic subjects. In particular, regarding RBP3, as it does not appear to be expressed in any other tissues than the eye, systemic administration is not expected to cause significant toxicity.

Other methods of treatment comprise preventing the degradation of a factor listed in Table 6 or 8, such as RBP3. Yet other methods include administering an agent that increases the expression of a factor in Table 6 or 8 or that reduces the expression of a risk factor listed in Table 7 or 9. An agent may be a small molecule, e.g., a small molecule that activates the promoter of the factor. In certain embodiments, an agent for treating a subject as described herein is an agent that increases the activity of a factor in Table 6 or 8 or reduces the activity of a factor in Table 7 or 9.

The present disclosure also contemplates the use of gene therapy methods, e.g., to administer a nucleic acid encoding one or more of the factors (e.g., protective factors) or nucleic acids inhibiting the expression or activity of a DR or DN risk factor disclosed herein to a subject. For example, nucleic acids encoding a protein disclosed in Table 6 and/or 8, or a variant thereof, or a nucleic acid encoding the protein that increases the expression, level or activity, of one or more of the factors disclosed in Tables 6 and/or 8 can be incorporated into a gene construct to be used as a part of a gene therapy protocol.

The invention includes targeted expression vectors for in vivo transfection and expression of a polynucleotide that encodes a polypeptide disclosed in Table 6 and/or 8, or an active fragment thereof, in particular cell types, for cells of the eye and/or kidney. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986)).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein (e.g., a nucleic acid encoding a polypeptide disclosed in Table 6 or 8, or an active fragment thereof, and/or a nucleic acid that increases the expression and/or activity of a polynucleotide that encodes a polypeptide disclosed in Table 6 or 8 or a nucleic acid that inhibits a protein in Table 7 or 9) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21):1867-74 (2000).

In some embodiments, an agent, e.g., a gene encoding a factor described herein, e.g., a polynucleotide that encodes a polypeptide disclosed in Table 6 or 8, or an active fragment thereof, or an agent that inhibits the expression or activity of a factor in Table 7 or 9, is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

In some embodiments, the present disclosure includes the use of agonists of any one or more of the factors disclosed in Tables 6 and/or 8. In some embodiments, suitable agonists can increase the expression and/or activity of one or more of the factors disclosed in Tables 6 and/or 8, e.g., by about 2-fold, 3-fold, 4-fold, 5-fold, or more.

In some embodiments, the present disclosure includes the use of antagonists of any one or more of the factors disclosed in Tables 7 and/or 9. In some embodiments, suitable antagonists can decrease the expression and/or activity of one or more of the factors disclosed in Tables 7 and/or 9, e.g., by about 2-fold, 3-fold, 4-fold, 5-fold, or more.

Many of the factors disclosed herein are referenced by the International Protein Index (IPI) number assigned to them. The sequences associated with each of the disclosed IPI numbers are publically available and can be obtained and/or viewed, for example, using the European Institute for Bioinformatics website available at world wide web address ebi.ac.uk. Other suitable websites are also known in the art.

Subject Selection

The term "subject" is used throughout the specification to describe an animal, human or non-human, to whom treatment according to the methods of the present invention is provided.

The methods disclosed herein can include selecting a subject for treatment. For example, a subject can be selected if the subject has or is at risk for developing DR and/or DN, e.g., a subject having diabetes, e.g., type 1 or type 2 diabetes, or a subject who is prediabetic, e.g., having metabolic syndrome, insulin resistance, hyperglycemia, hyperlipidemia or a subject who is overweight or obese, e.g., having a BMI≥25. In some instances, a subject can be selected if the subject has or is at risk for developing type 1 and/or type 2 diabetes. In some instances, a subject can be selected if the subject is taking or will take insulin, e.g., to treat diabetes.

Routes of Administration

One or more (e.g., 1, 2, 3, 4, 5, 6, 7, 8, 9, 10, 11, 12, 13, 14, 15, 16, 17, 18, 19, 20, or more, including all) of the agents, such as factors disclosed herein (e.g., disclosed in Tables 6 and/or 8) or agents inhibiting a factor of Table 7 or 9, can be administered alone or as a pharmaceutical composition (disclosed below) using any mode of administration, e.g., including any mode of administration that results in a therapeutically effective level in the eye (for DR) and/or the kidney (for DN). In some instances, a therapeutically effective level is an amount or level that results in one or more of the symptoms of DR and/or DN being ameliorated or otherwise beneficially altered. For the treatment of DR, an exemplary route of administration can include local administration into or onto the eye. For the treatment of DN, an exemplary route of administration can include local administration to the kidney. Other exemplary modes of administration suitable for either DR or DN include, but are not limited to, oral, parenteral, inhalation (e.g., as a spray), topical, rectal, nasal, buccal, vaginal, and/or via an implanted reservoir.

The term parenteral as used herein includes subcutaneous, intracutaneous, intravenous, intramuscular, intraarticular, intraarterial, intrasynovial, intrasternal, intrathecal, intralesional and intracranial injection or infusion techniques. Alternatively or in addition, the present invention may be administered according to any of the Food and Drug Administration approved methods, for example, as described in CDER Data Standards Manual, version number 004 (which is available at fda.give/cder/dsm/DRG/drg00301.htm). Where application over a period of time is advisable or desirable, the compositions of the invention can be placed in sustained released formulations (e.g., hydrogels) or implantable devices (e.g., implantable pumps).

Pharmaceutical Compositions

One or more (e.g., 1, 2, 3, 4, 5, 6, 7, 8, 9, 10, 11, 12, 13, 14, 15, 16, 17, 18, 19, 20, or more, including all) of the agents, e.g., factors disclosed herein (e.g., disclosed in Tables 6 and 8) or inhibitors of factors in Table 7 or 9, can be formulated in or as pharmaceutical compositions. Such pharmaceutical compositions can contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

In some cases, pharmaceutical compositions containing one or more factors can be formulated according to the intended method of administration.

Pharmaceutical compositions containing one or more factors can be formulated in a conventional manner using one or more physiologically acceptable carriers or excipients. The nature of the pharmaceutical compositions for administration is dependent on the mode of administration and can readily be determined by one of ordinary skill in the art. In addition, methods for making such formulations are well known and can be found in, for example, Remington's Pharmaceutical Sciences, 18th Ed., Gennaro, ed., Mack Publishing Co., Easton, Pa., 1990. In some embodiments, the pharmaceutical composition is sterile or sterilizable.

Pharmaceutical compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol.

In some embodiments, pharmaceutical compositions can be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the composition may be in powder form for constitution with a suitable vehicle, for example, sterile pyrogen-free water, before use. Agents that enhance delivery into a cell can be used as well, e.g., liposomes or micelles.

In addition to the formulations described previously, the compositions can also be formulated as a depot preparation. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions can also take the form of tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

The methods herein contemplate administration of an effective amount of compound or compound composition to achieve the desired or stated effect. Toxicity and therapeutic efficacy of the compounds and pharmaceutical compositions described herein can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans.

The formulations and routes of administration can be tailored to the disease or disorder being treated, and for the specific human being treated. A subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

Generally the dosage facilitates an intended purpose for both prophylaxis and treatment without undesirable side effects, such as toxicity, irritation or allergic response.

Although individual needs may vary, the determination of optimal ranges for effective amounts of formulations is within the skill of the art. Human doses can readily be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

Subject Evaluation

The methods can also include monitoring or evaluating the subject during and after treatment to determine the efficacy of the treatment, and, if necessary, adjusting treatment (e.g., by altering the composition, by increasing the dose of a single administration of the composition, by increasing the number of doses of the composition administered per day, and/or by increasing the number of days the composition is administered) to improve efficacy. Monitoring or evaluating the subject can include identifying a suitable marker of disease prior to commencing treatment and optionally recording the marker, and comparing the identified or recorded marker to the same marker during and/or after treatment. Suitable markers can include one or more symptoms of the subject's disease. Suitable markers also include one or more of the factors described in Tables 6, 8, 7 and 9. Adjustment of treatment would be recommended where the marker is a symptom of disease and comparison of the marker during or after treatment with the marker prior to treatment revealed either no change in the marker or an increase in the marker. Conversely, adjustment of treatment may not be required using the same markers where an increase in the marker is observed.

EXAMPLES

The invention is further described in the following examples, which do not limit the scope of the invention described in the claims.

Example 1

Identification of Protective DR Factors

Evidence that diabetic retinal pathologies can be halted has been documented by the Joslin 50-Year Medalist Study (Keenan et al., Diabetes Care. 2007 August; 30(8):1995-7. Epub 2007 May 16). Population characteristics for these subjects are shown in Table 1.

TABLE 1

Characteristics of Medalist Study participants.

| | % (n); mean ± std dev |
|---|---|
| Male (%) | 47.0% (192) |
| HbA1c (%) | 7.3% ± 1.1 |
| Age (years) | 67.2 ± 7.4 |
| Age at diagnosis (years) | 11.0 ± 6.5 |
| Duration (years) | 56.2 ± 5.8 |
| BMI (kg/m$^2$) | 26.0 ± 5.1 |
| C-peptide (nmol/L) | 0.07 ± 0.12 |

TABLE 1-continued

Characteristics of Medalist Study participants.

| | % (n); mean ± std dev |
|---|---|
| Cholesterol (mmol/L) | 4.2 ± 0.9 |
| HDLc (mmol/L) | 1.6 ± 0.5 |
| LDL (mmol/L) | 2.2 ± 0.6 |
| Triglycerides (mmol/L) | 0.9 ± 0.5 |
| Insulin dose (u/kg) | 0.46 ± 0.2 |
| Family History  Any DM | 29.7 (122) |
|   T1DM | 12.9 (53) |
| DR3 | 38.8 (116) |
| DR4 | 52.0 (156) |
| DR3 or DR4 | 93.7 (295) |
| DR3/4 | 39.1 (118) |
| IA2 or GAD | 29.7 (111) |
| IA2 | 14.9 (56) |
| GAD | 18.4 (69) |
| PDR | 55 (163) |
| Microalbuminuria (ACR <7.91) | 13.1 (45) |
| Neuropathy (MNSI >2) | 60.6 (183) |
| CVD | 48.3 (160) |

This study characterizes a number of individuals collectively referred to herein as 'Medalists' who have lived with for 50 or more years with type 1 diabetes (T1DM) by clinical exam, medical history and extensive chemistries.

Retinal pathology was documented by dilated fundus examination and fundus photography. The degree of renal disease was assessed through measurements of albumin, creatinine, cystatin C and estimated glomerular filtration rate (eGFR). After characterizing over 500 Medalists, a bimodal distribution of DR was observed with 50% of the Medalists having none to moderate nonproliferative DR and 50% having quiescent PDR (FIG. 1 and Table 1). Surprisingly, standard risk factors, including duration of diabetes and HbA1C levels, were not associated with severity.

Figure 2:
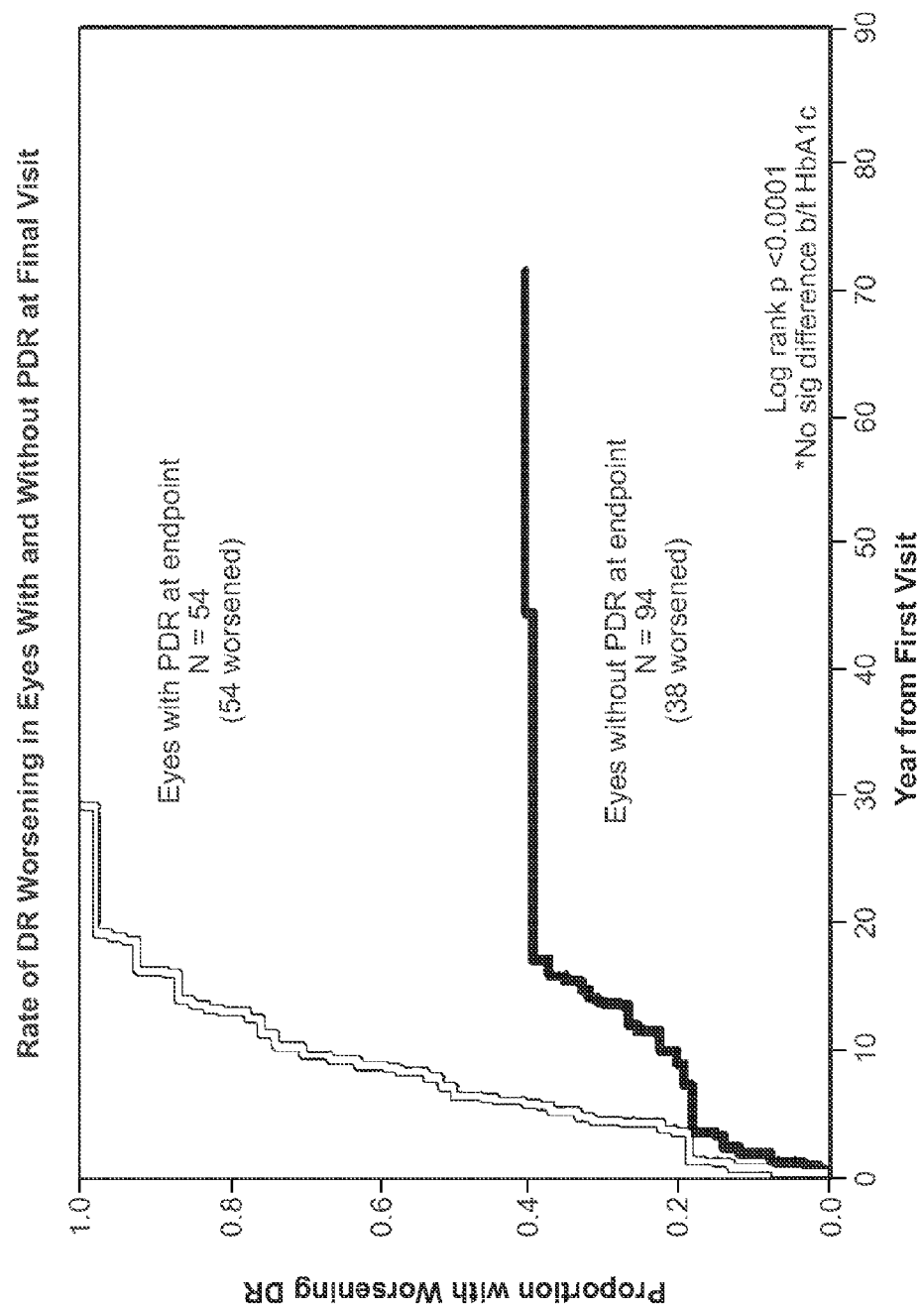
FIG. 2 is a line graph showing the rate of DR worsening in eyes with and without PDR at the final visit.

A subset of 97 Medalists has been followed with multiple ophthalmic examinations. Analysis of DR progression showed that 47.4% of eyes without proliferative DR (PDR) at baseline progressed to PDR, with a median time to progression to PDR of 38.4 years. The majority of Medalists who did not progress to PDR developed mild to moderate non-proliferative DR (NPDR) over a median follow-up of 20.6 years. Interestingly, of the eyes that did not develop PDR, all but one eye stopped progressing after 17 years of follow-up (FIG. 2). Over the last two years we have been collaborating with the network for Pancreatic Organ Donors with Diabetes (nPOD) to procure tissues from Medalists after they have passed away. Organ donations have been obtained from 11 Medalists, including whole eyes, kidneys, pancreas and skin. During their initial study visit we obtained specimens of DNA, serum, plasma, and urine.

In the present experiments, samples were taken from eight eyes: three with no to moderate NPDR, four with PDR, and one ungradeable (due to scatter laser performed for non-diabetic pathology) as determined by grading of fundus photographs. Retinal pathology was assessed using standard methods. For proteomic analysis, retinal and vitreous specimens were isolated and isolated using mass spectrometry methods as previously described (Gao et al., J Proteome Res. 2008; 7:2516-25; Gao et al., Nat Med. 2007; 13:181-8). Initial analysis of these eight eyes by mass spectrometry identified over 450 proteins. Based on a minimum 1.5 fold increase and significance level of at least 0.1, 26 proteins were found to be higher in the vitreous of Medalists who have no to moderate NPDR compared to those with PDR. Interestingly, pathway analysis indicated that 6/26 of these proteins have anti-angiogenic actions, whereas, only 1/26 have anti-oxidative stress properties and 8/26 are adhesion proteins. (Table 2).

TABLE 2

Protective genes or proteins in Eye vitreous

G-Protein

| | |
|---|---|
| APLP2 | amyloid beta (A4) precursor-like protein 2 G-protein coupled receptor protein signaling pathway |

Prostaglandin Enzyme

| | |
|---|---|
| PTGDS | prostaglandin D2 synthase 21 kDa (brain) glutathione-independent prostaglandin D synthase, PGH2-> PGD2 also fatty acid biosynthetic process | associate with Basement Membrane

| | |
|---|---|
| B3GNT1 | UDP-GlcNAc:betaGal beta-1,3-N-acetylglucosaminyltransferase 1 type II transmembrane protein, integral to Golgi membrane |

Complement

| | |
|---|---|
| C5 | Complement C5 |
| C6 | Complement C6 |
| A2M | Alpha-2-macroglobulin a protease inhibitor and cytokine transporter |

Growth/tumor suppressor gene

| | |
|---|---|
| DKK3 | |
| WIF1 | |

Ig superfamily

Rheumatoid factor
C6 light chain
IGLV1-40
Ig kappa chain V-
IV region Len
IGHM

Cytokine

FAM3C
SERPINF1(PEDF)
A2M

Adhesion protein

| | |
|---|---|
| CLSTN1 | |
| SPARCL1 | |
| CDH2 | cadherin 2, type 1, N-cadherin |
| SPP1 | secreted phosphoprotein 1 ECM-receptor interaction, Focal adhesion, Toll-like receptor signaling pathway, Signaling by PDGF, Integrin cell surface interactions, osteoblast differentiation |
| NRCAM | |
| APP | |

Protease inhibition

| | |
|---|---|
| A2M | Alpha-2-macroglobulin a protease inhibitor and cytokine transporter |
| SERPINF1(PEDF) | |
| PCSK1N | |
| CST3 | cystatin C |
| CPE | Carboxypeptidase E |
| APP | serine-type endopeptidase inhibitor activity |

Lipid metabolism

| | |
|---|---|
| ASAH1 | Acid ceramidase |
| APOE | |

Oxidative Stress

GPX3

TABLE 2-continued

Protective genes or proteins in Eye vitreous

Not grouped

ABI3BP
CUTA
SEZ

Clinical characterization of the Medalists and histopathologic and proteomic analysis of their tissues has enabled us to identify new biomarkers for progression to PDR for diabetic patients with shorter duration disease. Furthermore, these protective factors against the progression of DR are potential therapeutic targets.

These potential "protective" and "risk" factors identified from the vitreous and retinas of Medalist patients are secondarily screened using (intraocular) aqueous fluid and plasma from a population of both type 1 and 2 diabetic patients who are having cataract extraction, to determine the levels of biomarkers in more readily accessible fluids such as plasma, and correlate the levels in plasma to those in intraocular fluids. There is also a small group of nondiabetic individuals that undergoes cataract surgery at BEI each year. It is standard procedure to discard aqueous fluid during cataract surgery; this discarded fluid is used to assess the presence of candidate protective/risk factors. Additionally, we will obtain medical history, physical exam, and blood samples to characterize the non-Medalists in the same manner as the Medalist participants. Using this case-control approach, the differential presence of candidates can be assessed in the aqueous, plasma and potentially urine across the stages of DR.

Example 2

Identification of Protective DN Factors

Nine kidney samples from the Medalists were analyzed by mass spectrometry as previously described (Gao et al., J Proteome Res. 2008; 7:2516-25; Gao et al. Nat Med. 2007; 13:181-8). Using the results from the proteomic analyses and correlated pathology derived from the renal glomeruli, we found that the expression of 14 proteins are significantly (1.5 fold) greater in kidneys without disease vs. those with class II and III levels of nephropathy. The proteins are listed in Table 3.

TABLE 3

Protective genes or proteins in Renal Glomeruli

Lipid Metabolism

| | |
|---|---|
| APOA1BP | Isoform 2 of Apolipoprotein A-I-binding protein precursor interacts with apolipoprotein A-I (apoA-I), the major apolipoprotein of high-density lipoproteins (HDLs) |

Oxidation reduction/ Oxidative Stree

| | |
|---|---|
| MOSC2 | Isoform 1 of MOSC domain-containing protein 2, mitochondrial precursor (mt) |
| HPX | Hemopexin precursor |
| GPX3 | glycoprotein, binds heme Glutathione peroxidase 3 precursor detoxification of hydrogen peroxide |
| GSTT1 | Glutathione S-transferase theta 1 |
| PRDX1 | peroxiredoxin 1 antioxidant enzymes, reduce hydrogen peroxide and alkyl hydroperoxides |

TABLE 3-continued

Protective genes or proteins in Renal Glomeruli

| | |
|---|---|
| HADH | Isoform 2 of Hydroxyacyl-coenzyme A dehydrogenase, mitochondrial precursor (mt) also fatty acid metabolism |
| SCCPDH | saccharopine dehydrogenase (putative) oxidoreductase activity (mt) |
| Purine metabolism | |
| HPRT1 | hypoxanthine phosphoribosyltransferase 1 |
| Basement membrane | |
| COL18A1 | collagen, type XVIII, alpha 1 |
| Mitochondrial metabolism/enymes | |
| MOSC2 | |
| HADH | |
| SCCPDH | |
| GATM | Glycine amidinotransferase (L-arginine:glycine amidinotransferase) |
| | Metabolism of amino acids and derivatives |
| AGMAT | agmatine ureohydrolase (agmatinase) |
| | Metabolism of amino acids and derivatives |
| CS | citrate synthase |
| Glucose metabolism | |
| GNPDA1 | glucosamine-6-phosphate deaminase 1 |
| | Amino sugar and nucleotide sugar metabolism |

Validation of the proteins identified through comparison of those with and without DN will be done using samples of urine, plasma and serum from the Joslin Natural History of Microalbuminuria Studies. The validation study is a case-control testing the hypothesis of a significantly lower level of the factor of interest being present in fast progressors, defined as those who have had a greater than 7% eGFR loss of per year over a 10 year period within 15 year duration compared to those with chronic kidney disease classifications 1, 2, or 3.

Example 3

Plasma Levels of DN Protective Factor GPX3 Correlate Positively with the GFR

Candidates identified by our proteomic analysis of the vitreous and kidney are measured in the plasma of normal and type 1 diabetic patients to validate the relationship with protection against DR/DN, and to examine whether there is a temporal relationship with progression of DR/DN.

Figure 3:
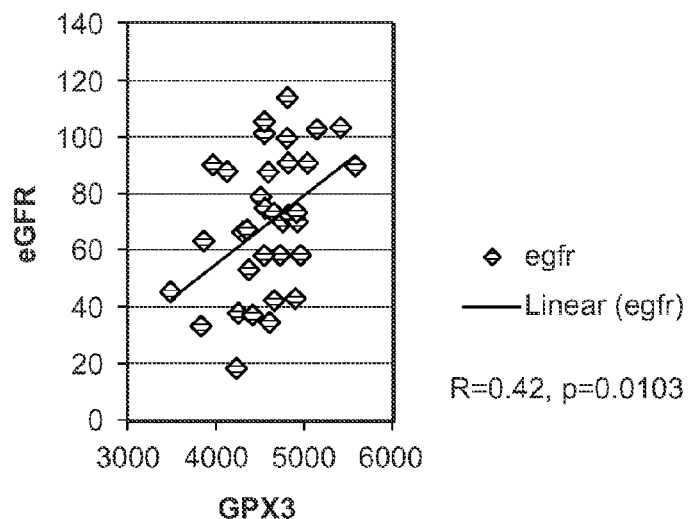
FIG. 3 is a scatter plot showing the correlation of plasma GPX3 Level to estimated GFR in a subset of 50 year medalist subjects. GFR was estimated using equation from Stevens et al, Am J Kidney Dis 2008; 51: 395-40.

GPX3, which was identified as a biomarker in both the vitreous and kidney, a secreted enzyme and is involved in neutralizing hydroxides and preventing lipid peroxidation, was measured plasma GPX3 levels by ELISA method in 40 Medalists and a positive correlation was observed between the level of GPX3 and estimated GFR calculated by cystatin C (FIG. 3).

The results described herein are corroborated by reports in the literature. PEDF, an anti-angiogenic protein representing a major pathway of protective factors identified in the vitreous proteomic study (Table 2), has been assayed in plasma. Levels of PEDF in plasma among those with PDR have been found at 5.3±5.1 ng/mL and among those without at 7.7±6.1 ng/mL (Matsuyama et al., Mol Vis. 2008 May 28; 14:992-6). A sample size of 100 cases and 100 controls yields a power of 83% with p≤0.05). In aqueous Yoshida et al report a mean PEDF level of 1.8±0.2 ng/mL among those with DR and 6.4±0.8 ng/mL among those without (Br J Ophthalmol. 2007 September; 91(9):1133-4).

Example 4

Identification of Factors that Protect Against DR

Figure 4:
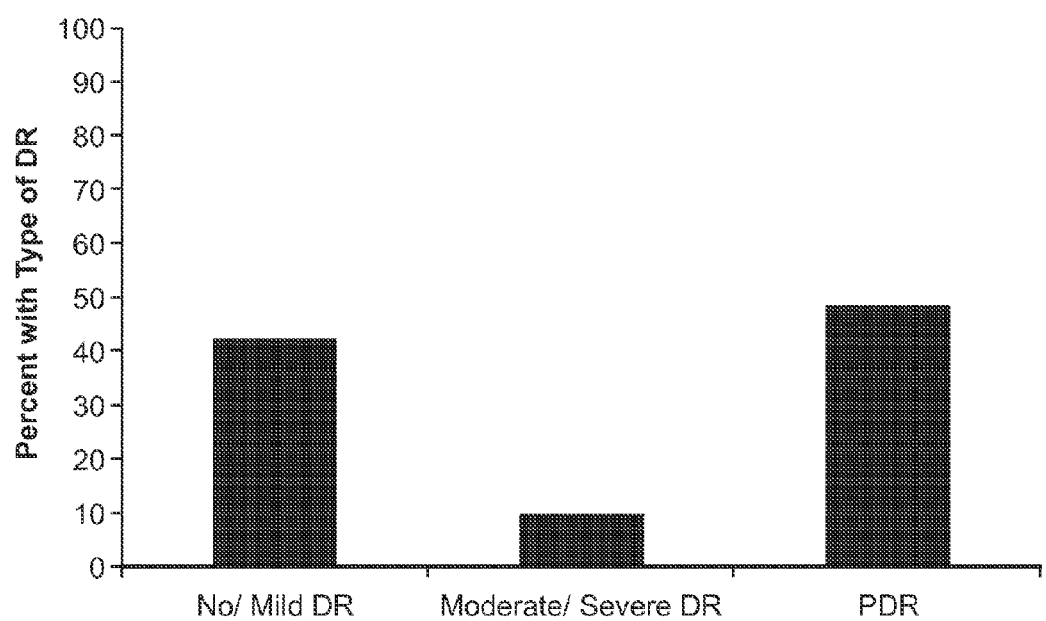
FIG. 4 is a bar graph showing the prevalence of DR status (no DR or mild DR, moderate to severe DR, and proliferative DR ((PDR) advanced disease)) among the subjects described in Example 4.

The prevalence of DR in the Medalists evaluated is shown in FIG. 4. Candidate factors that protect against DR were identified by comparing the levels or expression of factors in individuals with DR and those without DR. Factors with a statistically significant difference in expression between the individuals with DR and those without DR were selected. A total of 700 candidate factors were selected. Further statistical analysis was then applied to select protective factors from the candidate factors. After applying kruskal-wallis statistical analysis, a total of 22 protective factors (the first 22 factors in the Table, i.e., those above the black line) and 3 risk factors (the last three lines in the Table, i.e., those under the black line) were identified, as shown in Table 4 and FIG. 7. FIG. 7 lists only the protective factors. The criteria of the selection for the protective factors was p value <0.05, and expression level increased >=1.5 fold in individuals without DR (i.e. no to mild NPDR).

The analysis was performed essentially as follows. The protein analysis was done using a label-free quantitative analysis of 1D PAGE-LC/MS/MS-based proteomics. Soluble proteins from vitreous tissues of 50-Year Medalists were loaded onto 10% acrylamide protein gels for separations in 1-D gel electrophoresis. We loaded 50 uL (micro liter) of vitreous fluid with sample buffer in each sample lane on the gel. Then the gel was stained with Coomassie Blue. Each lane of gel was then cut into 40 slices. The 40 slices were digested in separate tubes by trypsin. These digested protein gel slices were then loaded into an LC machine for the later MS/MS analysis.

The number of peptide hits was obtained from the "MS manager," software previously developed by Benbo Gao (Gao B et al. Mol Cell Proteomics 2008; 7:2399-2409). MS manager is designed based on the PHP-MySQL-Apache platform. It compiles the search results from SEQUEST and X!Tandem of MS/MS data, and then parses these results into the MySQL database. After applying the algorithm for filtering proteins and combining the IPI identifier, a final report of identified proteins is generated in a table with peptide hit numbers. The results are shown in Table 4 below.

TABLE 4

| Name of DR protective factor | DR grade Accession Nos. | Protective Factors for DR | | | | | | | | | | | | | | | |
|---|---|---|---|---|---|---|---|---|---|---|---|---|---|---|---|---|---|
| | | 2 262CD | 3 600KS | 2 600KD | 0 269CS | 0 269CD | No-mild NPDR Average | 8 629TD | 8 629TS | 8 482SS | 8 482SD | 8 365LD | 8 220WS | 8 220WD | PDR Average | Fold increase | P value |
| B3GNT1 N-acetyllactosaminide beta-1,3-Nacetylglucosaminyl transferase | IPI00009997 | 7 | 7 | 13 | 6 | 0 | 6.6 | 0 | 0 | 0 | 0 | 0 | 0 | 0 | 0.0 | ∞ | 0.006687 |
| CHL1 Isoform 1 of Neural cell adhesion molecule L1-like protein precursor | IPI00783390 | 3 | 4 | 3 | 5 | 0 | 3.0 | 0 | 0 | 0 | 0 | 0 | 0 | 0 | 0.0 | ∞ | 0.006687 |
| LRP2 Low-density lipoprotein receptor-related protein 2 precursor | IPI00024292 | 9 | 5 | 6 | 2 | 0 | 4.4 | 0 | 0 | 0 | 0 | 0 | 0 | 0 | 0.0 | ∞ | 0.006824 |
| CD14 Monocyte differentiation antigen CD14 precursor | IPI00029260 | 4 | 2 | 0 | 0 | 2 | 1.6 | 0 | 0 | 0 | 0 | 0 | 0 | 0 | 0.0 | ∞ | 0.024768 |
| TNR Isoform 2 of Tenascin-R precursor | IPI00554760 | 11 | 2 | 0 | 3 | 0 | 3.2 | 0 | 0 | 0 | 0 | 0 | 0 | 0 | 0.0 | ∞ | 0.025207 |
| BTD Uncharacterized protein BTD (Fragment) | IPI00744685 | 3 | 0 | 6 | 2 | 0 | 2.2 | 0 | 0 | 0 | 0 | 0 | 0 | 0 | 0.0 | ∞ | 0.025207 |
| IGLV1-40 V1-13 protein (Fragment) | IPI00789259 | 3 | 9 | 6 | 0 | 0 | 3.6 | 0 | 0 | 0 | 0 | 0 | 0 | 0 | 0.0 | ∞ | 0.025207 |
| COL18A1 Isoform 2 of Collagen alpha-1(XVIII) chain precursor | IPI00022822 | 12 | 0 | 3 | 4 | 5 | 4.8 | 0 | 0 | 0 | 2 | 0 | 0 | 0 | 0.3 | 16.80 | 0.014495 |
| SEZ6 Isoform 3 of Seizure protein 6 homolog precursor | IPI00748395 | 9 | 4 | 6 | 4 | 0 | 4.6 | 0 | 0 | 0 | 0 | 0 | 3 | 0 | 0.4 | 10.73 | 0.014282 |
| APLP1 amyloid precursor-like protein 1 isoform 1 precursor | IPI00607600 | 0 | 8 | 8 | 6 | 4 | 5.2 | 0 | 0 | 0 | 0 | 0 | 4 | 0 | 0.6 | 9.10 | 0.018053 |
| HSPG2 Basement membrane-specific heparan sulfate proteoglycan core protein precursor | IPI00024284 | 15 | 4 | 5 | 2 | 0 | 5.2 | 0 | 2 | 2 | 2 | 0 | 0 | 0 | 0.6 | 9.10 | 0.035993 |
| FCGBP IgGFc-binding protein precursor | IPI00242956 | 66 | 18 | 29 | 5 | 6 | 24.8 | 0 | 5 | 8 | 0 | 2 | 8 | 0 | 3.3 | 7.55 | 0.032868 |

TABLE 4-continued

| Name of DR protective factor | DR grade Accession Nos. | 2 262CD | 3 600KS | 2 600KD | 0 269CS | 0 269CD | No-mild NPDR Average | 8 629TD | 8 629TS | 8 482SS | 8 482SD | 8 365LD | 8 220WS | 8 220WD | PDR Average | Fold increase | P value |
|---|---|---|---|---|---|---|---|---|---|---|---|---|---|---|---|---|---|
| APLP2 Isoform 1 of Amyloid-like protein 2 precursor | IPI00031030 | 47 | 43 | 42 | 18 | 14 | 32.8 | 0 | 4 | 6 | 18 | 0 | 6 | 0 | 4.9 | 6.75 | 0.008637 |
| TAGLN Transgelin | IPI00216138 | 0 | 2 | 4 | 39 | 30 | 15.0 | 0 | 0 | 0 | 0 | 25 | 0 | 0 | 3.6 | 4.20 | 0.037289 |
| AGT Angiotensinogen precursor | IPI00032220 | 5 | 17 | 19 | 15 | 19 | 15.0 | 7 | 3 | 8 | 7 | 0 | 4 | 2 | 4.4 | 3.39 | 0.018124 |
| C9 Complement component C9 precursor | IPI00023395 | 6 | 12 | 8 | 18 | 12 | 11.2 | 5 | 4 | 0 | 6 | 0 | 9 | 0 | 3.4 | 3.27 | 0.013818 |
| Autotaxin isoform gamma | IPI00878576 | 16 | 14 | 18 | 13 | 14 | 15.0 | 3 | 0 | 6 | 7 | 0 | 19 | 2 | 5.3 | 2.84 | 0.041637 |
| RBP3 Interphotoreceptor retinoid-binding protein precursor | IPI00022337 | 560 | 583 | 474 | 609 | 611 | 567.4 | 62 | 57 | 155 | 269 | 286 | 401 | 235 | 209.3 | 2.71 | 0.004483 |
| Transthyretin | IPI00855916 | 534 | 462 | 1238 | 234 | 199 | 533.4 | 173 | 111 | 200 | 134 | 256 | 363 | 155 | 198.9 | 2.68 | 0.042357 |
| CST3; CST2 Cystatin-C precursor | IPI00033293 | 51 | 49 | 62 | 34 | 14 | 42.0 | 18 | 21 | 17 | 16 | 9 | 31 | 8 | 17.1 | 2.45 | 0.042357 |
| A2M Alpha-2-macroglobulin | IPI00478003 | 187 | 223 | 285 | 218 | 172 | 217.0 | 42 | 34 | 124 | 108 | 130 | 238 | 49 | 103.6 | 2.10 | 0.028351 |
| CP Ceruloplasmin precursor | IPI00017601 | 424 | 264 | 271 | 363 | 317 | 327.8 | 276 | 200 | 87 | 207 | 243 | 234 | 203 | 207.1 | 1.58 | 0.011829 |
| CLEC3B Putative uncharacterized protein DKFZp686H17246 | IPI00792115 | 0 | 3 | 4 | 0 | 0 | 1.4 | 10 | 12 | 3 | 10 | 3 | 23 | 22 | 11.9 | 0.12 | 0.016723 |
| AFM Afamin precursor | IPI00019943 | 0 | 0 | 0 | 0 | 0 | 0.0 | 0 | 3 | 3 | 6 | 0 | 13 | 13 | 5.4 | 0.00 | 0.022991 |
| CFD Complement factor D preproprotein | IPI00165972 | 0 | 0 | 0 | 0 | 0 | 0.0 | 6 | 4 | 0 | 5 | 0 | 5 | 5 | 3.6 | 0.00 | 0.022394 |

The first column in Table 4 shows the names of DR protective factors. The second column shows the International Protein Index numbers (IPI numbers) of the protective factor proteins. These accession numbers were retrieved from mass spectrometry analysis result, mapped to EMBI-EBI IPI database. Columns 3-7 and columns 9-15 show the peptide hits of each factor (reflecting the expression level) from each vitreous sample. Columns 3-7 are hits in samples from subjects having no-mild NPDR, and columns 9-15 are hits from subjects having PDR. The first line of the Table refers to the grade of the DR from which each of the samples were obtained (e.g., "2," "3," and "0," refer to NPDR grades 2, 3 and 0, respectively). The line listing, e.g., "262C D," refers to the name of the samples. Column 8 is the average number of hits in no-mild NPDR samples, compiled from columns 3-7 for each factor. Column 16 is the average number of hits in PDR samples, complied from columns 9-15. Column 17 shows the fold difference between the average number of hits in the no-mild NPDR samples (column 8) to the average number of hits in the PDR samples (column 16) for each factor. The fold increase column shows that the factors are expressed at higher levels in type 1 diabetic individuals without DR compared to those with DR.

Example 5

Identification of Factors that Protect Against DN or Increase the Risk of DN

Figure 5:
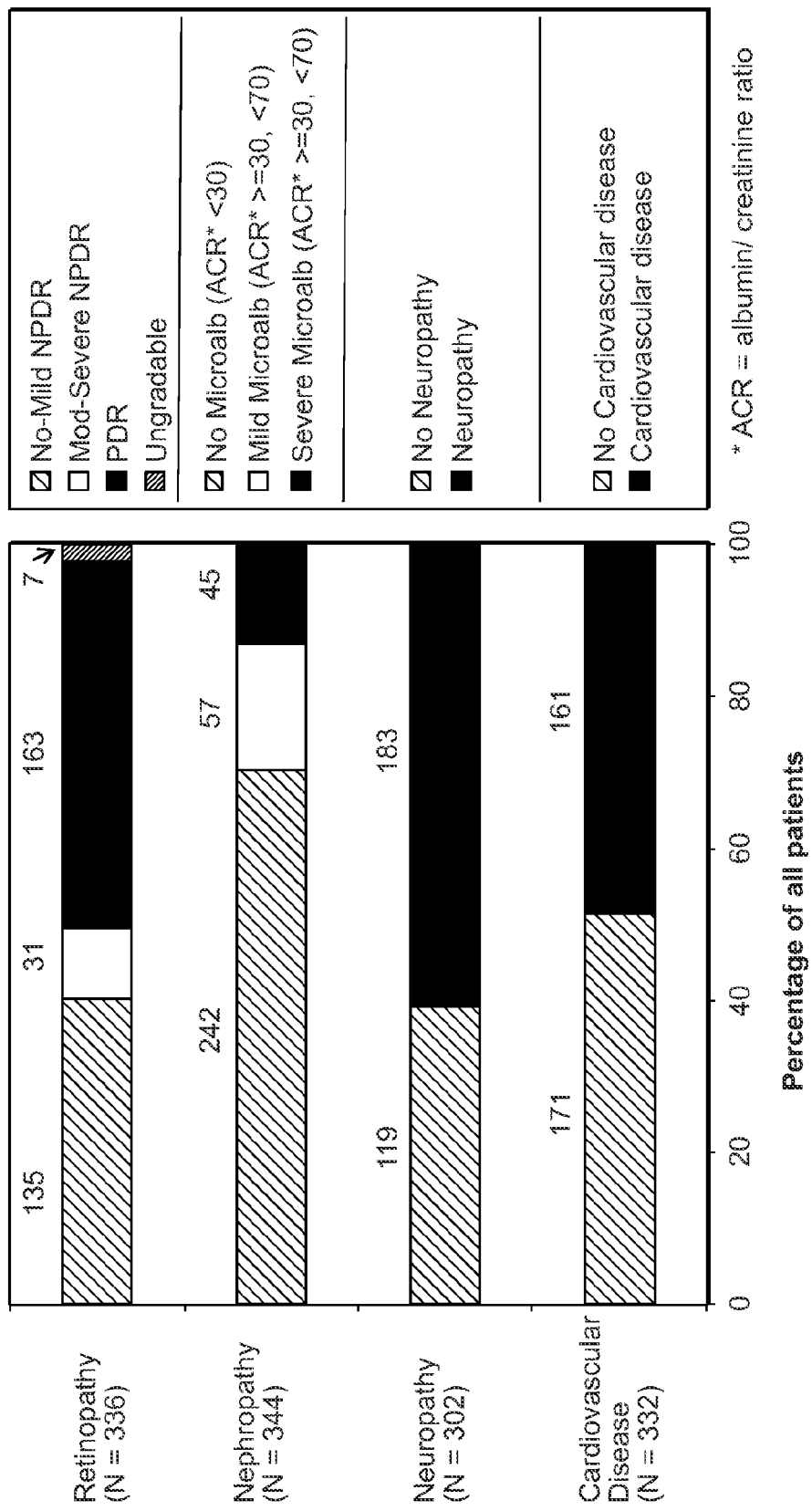
FIG. 5 is a chart showing microvascular and macrovascular complications in the subjects disclosed in Examples 4-5.

Complications observed in Medalists are shown in FIG. 5 and a summary of clinical characteristics in Medalists is shown in FIG. 6. Candidate factors that protect against DN were identified by comparing the levels or expression of factors in individuals with DN and those without DN. Factors with a statistically significant difference in expression between the individuals with DN and those without DN were selected. A total of 1709 candidate factors were selected.

Further statistical analysis was then applied to select protective factors from the candidate factors. After applying kruskal-wallis statistical analysis, a total of 15 protective factors (first 15 entries in Table 5, i.e., those above the line in the middle of the Table) and 17 risk factors (bottom 17 entries in Table 5, i.e., those below the line in the middle of the table) were identified, as shown in Table 5 and FIG. 8. FIG. 8 only lists the protective factors. The criteria of the selection for protective factors was p value <0.05, and expression level increased >=1.5 fold in individuals without DN. The criteria of the selection for risk factors was p value <0.05, and expression level increased <=0.67 fold in individuals without DN (i.e., decreased >=1.5 fold in individuals with DN).

The analysis was performed essentially as follows. The protein analysis was done using a label-free quantitative analysis of 1D PAGE-LC/MS/MS-based proteomics. Soluble proteins from vitreous tissues of 50-Year Medalists were loaded onto 10% acrylamide protein gels for separations in 1-D gel electrophoresis. We loaded 200 ug (micro gram) of protein-prep (isolated by sieving, buffering, centrifuging, etc. several steps) with sample buffer in each sample lane on the gel. Then the gel was stained with Coomassie Blue. Each lane of gel was then cut into 40 slices. The 40 slices were digested in separate tubes by trypsin. These digested protein gel slices were then loaded into an LC machine for the later MS/MS analysis.

The number of peptide hits was obtained from the "MS manager," software previously developed by Benbo Gao (Gao B et al. Mol Cell Proteomics 2008; 7:2399-2409). MS manager is designed based on the PHP-MySQL-Apache platform. It compiles the search results from SEQUEST and X!Tandem of MS/MS data, and then parses these results into the MySQL database. After applying the algorithm for filtering proteins and combining the IPI identifier, a final report of identified proteins is generated in a table with peptide hit numbers. The results are shown in Table 5 below.

TABLE 5

Protective and Risk Factors for DN

| Accession | Protein Name | G7 | G4 | G3 | Clean Mean | G11 | G8 | G6 | G2 | G1 | G12 | G9 | G10 | G5 | Dz mean | Fold | P_KW |
|---|---|---|---|---|---|---|---|---|---|---|---|---|---|---|---|---|---|
| IPI00789618 | HDDC3 Isoform 1 of HD domain-containing protein 3 | 3 | 3 | 0 | 2.00 | 0 | 0 | 0 | 0 | 0 | 0 | 0 | 0 | 0 | 0.00 | #DIV/0! | 0.01 |
| IPI00178926 | IGJ immunoglobulin J chain | 0 | 45 | 18 | 21.00 | 0 | 0 | 0 | 0 | 0 | 0 | 0 | 8 | 0 | 0.89 | 23.63 | 0.04 |
| IPI00816799 | Rheumatoid factor D5 light chain (Fragment) | 7 | 4 | 0 | 3.67 | 0 | 3 | 0 | 0 | 0 | 0 | 0 | 0 | 0 | 0.33 | 11.00 | 0.04 |
| IPI00410215 | BPNT1 Isoform 2 of 3(2),5-bisphosphate nucleotidase 1 | 4 | 4 | 3 | 3.67 | 0 | 0 | 0 | 3 | 0 | 0 | 0 | 0 | 0 | 0.33 | 11.00 | 0.04 |
| IPI00009305 | GNPDA1 Glucosamine-6-phosphate isomerase | 4 | 3 | 4 | 3.67 | 0 | 0 | 5 | 0 | 4 | 0 | 0 | 0 | 0 | 0.56 | 6.60 | 0.02 |
| IPI00873466 | HPRT1 Uncharacterized protein HPRT1 | 6 | 4 | 5 | 5.00 | 3 | 3 | 5 | 0 | 0 | 0 | 0 | 0 | 0 | 1.22 | 4.09 | 0.02 |
| IPI00893316 | GSTT1 Glutathione S-transferase theta 1 | 30 | 23 | 20 | 24.33 | 4 | 10 | 25 | 11 | 4 | 0 | 0 | 0 | 9 | 7.00 | 3.48 | 0.03 |
| IPI00004101 | BHMT Betaine-homocysteine S-methyltransferase 1 | 182 | 74 | 118 | 124.67 | 17 | 105 | 60 | 78 | 29 | 16 | 10 | 0 | 33 | 38.67 | 3.22 | 0.03 |
| IPI00848298 | APOA1BP Isoform 2 of Apolipoprotein A-I-binding protein precursor | 8 | 8 | 10 | 8.67 | 0 | 3 | 4 | 4 | 5 | 0 | 4 | 3 | 6 | 3.22 | 2.69 | 0.01 |
| IPI00022488 | HPX Hemopexin precursor | 20 | 24 | 25 | 23.00 | 10 | 8 | 19 | 12 | 10 | 0 | 0 | 5 | 21 | 9.44 | 2.44 | 0.02 |
| IPI00218407 | ALDOB Fructose-bisphosphate aldolase B | 690 | 450 | 521 | 553.67 | 76 | 486 | 381 | 428 | 176 | 84 | 34 | 36 | 414 | 235.00 | 2.36 | 0.02 |
| IPI00305360 | AGMAT Agmatinase, mitochondrial precursor | 54 | 38 | 57 | 49.67 | 4 | 54 | 23 | 35 | 20 | 8 | 19 | 18 | 9 | 21.11 | 2.35 | 0.03 |
| IPI00792191 | GATM Glycine amidinotransferase (L-arginine:glycine amidinotransferase) variant | 213 | 177 | 222 | 204.00 | 32 | 207 | 111 | 149 | 64 | 60 | 74 | 108 | 57 | 95.78 | 2.13 | 0.02 |
| IPI00219446 | PEBP1 Phosphatidylethanolamine-binding protein 1 | 235 | 235 | 171 | 213.67 | 30 | 227 | 129 | 203 | 97 | 32 | 24 | 25 | 145 | 101.33 | 2.11 | 0.03 |
| IPI00025366 | CS Citrate synthase, mitochondrial precursor | 30 | 17 | 21 | 22.67 | 7 | 11 | 10 | 19 | 8 | 8 | 12 | 10 | 14 | 11.00 | 2.06 | 0.02 |
| IPI00554811 | TTLL3; ARPC4 Actin-related protein 2/3 complex subunit 4 | 4 | 4 | 5 | 4.33 | 16 | 8 | 6 | 7 | 6 | 12 | 17 | 5 | 4 | 9.00 | 0.48 | 0.04 |
| IPI00215948 | CTNNA1 Isoform 1 of Catenin alpha-1 | 5 | 13 | 3 | 7.00 | 26 | 6 | 17 | 14 | 16 | 20 | 18 | 22 | 11 | 16.67 | 0.42 | 0.03 |
| IPI00010796 | P4HB Protein disulfide-isomerase precursor | 26 | 8 | 23 | 19.00 | 65 | 29 | 39 | 26 | 48 | 74 | 52 | 57 | 22 | 45.78 | 0.42 | 0.04 |
| IPI00646415 | RAB14 20 kDa protein | 7 | 4 | 6 | 5.67 | 7 | 11 | 23 | 11 | 7 | 8 | 36 | 23 | 19 | 16.11 | 0.35 | 0.02 |
| IPI00025447 | EEF1A1 Elongation factor 1-alpha | 5 | 9 | 2 | 5.33 | 9 | 14 | 15 | 15 | 21 | 4 | 35 | 15 | 20 | 16.44 | 0.32 | 0.04 |
| IPI00413947 | AP1B1 Isoform B of AP-1 complex subunit beta-1 | 6 | 7 | 0 | 4.33 | 10 | 12 | 13 | 6 | 9 | 22 | 26 | 11 | 17 | 14.00 | 0.31 | 0.03 |
| IPI00009904 | PDIA4 Protein disulfide-isomerase A4 precursor | 8 | 6 | 4 | 6.00 | 23 | 16 | 24 | 15 | 16 | 17 | 19 | 27 | 20 | 19.67 | 0.31 | 0.01 |
| IPI00020599 | CALR Calreticulin precursor | 7 | 11 | 25 | 14.33 | 46 | 18 | 30 | 51 | 23 | 43 | 133 | 89 | 30 | 51.44 | 0.28 | 0.03 |
| IPI00401448 | ACSL1 Isoform 2 of Long-chain-fatty-acid-CoA ligase 1 | 3 | 2 | 3 | 2.67 | 22 | 11 | 4 | 6 | 0 | 11 | 28 | 4 | 4 | 10.00 | 0.27 | 0.05 |
| IPI00792916 | PRKCSH protein kinase C substrate 80K-H isoform 2 | 3 | 0 | 4 | 2.33 | 14 | 4 | 9 | 5 | 4 | 15 | 20 | 14 | 6 | 10.11 | 0.23 | 0.04 |
| IPI00025252 | PDIA3 Protein disulfide-isomerase A3 precursor | 5 | 12 | 8 | 8.33 | 72 | 12 | 29 | 26 | 30 | 30 | 85 | 58 | 27 | 41.00 | 0.20 | 0.02 |
| IPI00008274 | CAP1 Adenylyl cyclase-associated protein 1 | 5 | 0 | 0 | 1.67 | 13 | 4 | 10 | 4 | 7 | 16 | 15 | 6 | 5 | 8.89 | 0.19 | 0.04 |
| IPI00783726 | KTN1 kinectin 1 isoform b | 0 | 3 | 0 | 1.00 | 5 | 7 | 8 | 5 | 8 | 5 | 2 | 6 | 6 | 5.78 | 0.17 | 0.02 |
| IPI00025239 | NDUFS2 NADH dehydrogenase [ubiquinone] iron-sulfur protein 2, mitochondrial precursor | 0 | 3 | 0 | 1.00 | 20 | 4 | 5 | 3 | 2 | 12 | 3 | 10 | 4 | 7.00 | 0.14 | 0.03 |
| IPI00217943 | RAB6A Isoform 2 of Ras-related protein Rab-6A | 2 | 0 | 0 | 0.67 | 0 | 7 | 8 | 2 | 2 | 8 | 14 | 8 | 3 | 5.78 | 0.12 | 0.05 |
| IPI00016621 | AP2A2 Adaptor-related protein complex 2, alpha 2 subunit variant (Fragment) | 0 | 0 | 0 | 0.00 | 13 | 2 | 4 | 2 | 3 | 13 | 21 | 12 | 3 | 8.11 | 0.00 | 0.01 |
| IPI00025874 | RPN1 Dolichyl-diphosphooligosaccharide-protein glycosyltransferase 67 kDa subunit pre | 0 | 0 | 0 | 0.00 | 33 | 6 | 6 | 2 | 0 | 36 | 32 | 23 | 0 | 15.33 | 0.00 | 0.04 |

The first column in table 5 shows the International Protein Index numbers (IPI numbers) of the protective factor proteins. These accession numbers were retrieved from mass spectrometry analysis result, mapped to EMBI-EBI IPI database. The second column shows names of DN protective factors. Columns 3-5 and columns 7-15 show the peptide hits of each factor (reflecting the expression level) from each kidney sample. Columns 3-5 are hits in samples from subjects with no DN, and columns 7-15 are hits in samples from subjects with DN. The first line (listing, e.g., "G7") refers to the names of each sample. Column 6 ("Clean Mea") shows the average number of hits in the non-DN samples, compiled from columns 3-5 for each factor. Column 16 is the average number of hits in the DN samples, compiled from columns 9-15. Column 17 shows the fold difference between the average number of hits in the no-DN samples (column 6) to the average number of hits in the DN samples (column 16) for each factor. The fold column shows that the protective factors (factors 1-15, i.e., those above the line) are expressed at higher levels in type 1 diabetic individuals without DN compared to those with DR. It also shows that the risk factors (factors 16-32, i.e., those below the line) are expressed at lower levels in type 1 diabetic individuals without DN relative to those with DN.

Example 6

RBP3 Protein Levels are Higher in Vitreous of Medalists without PDR than in Vitreous from Medalists with PDR Vitreous from 6 eyes (4 Medalists) from the no to Mild-NPDR and 8 vitreous (5 Medalists) from the PDR groups. "No to mild NPDR" is characterized as Early Treatment Diabetic Retinopathy Study (ETDRS) severity levels 10-35, characterized by absent or less than severe hemorrhages/microaneurysms throughout the retina (Grading diabetic retinopathy from stereoscopic color fundus photographs—an extension of the modified Airlie House classification. ETDRS report number 10. Early Treatment Diabetic Retinopathy Study Research Group. Ophthalmology. 1991 May; 98(5 Suppl):786-806. PubMed PMID: 2062513; and Fundus photographic risk factors for progression of diabetic retinopathy. ETDRS report number 12. Early Treatment Diabetic Retinopathy Study Research Group. Ophthalmology. 1991 May; 98(5 Suppl):823-33. PubMed PMID: 2062515). 10 microliters of sonicated and centrifuged vitreous from each sample were loaded onto a 4-20% gel (Biorad) and transferred to a PVDF membrane (Immobilon-P). CystatinC, RBP3 and PTGDS (Abcam, 1:2000), Endophilin and Tenascin R (Santa Cruz 1:1000) were used for immunodetection. More specifically, rabbit anti-RBP3 (Abcam 101456) was used and Santa Cruz HRP anti-Rabbit was used as the secondary antibody for detection. The band density was analyzed using Image J, and p values represent student t test.

Figure 11B:
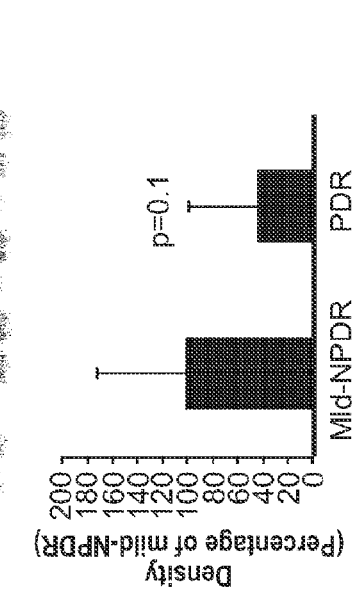
FIG. 11 A-C shows histograms with the values of RBP3 (A), PTGDS (B) and Cystatin C (C) protein levels in vitreous of Medalists without PDR versus in vitreous from Medalists with PDR, as measured via Western blots. "M" refers to Mild-NPDR and "P" refers to PDR.
Figure 11A:
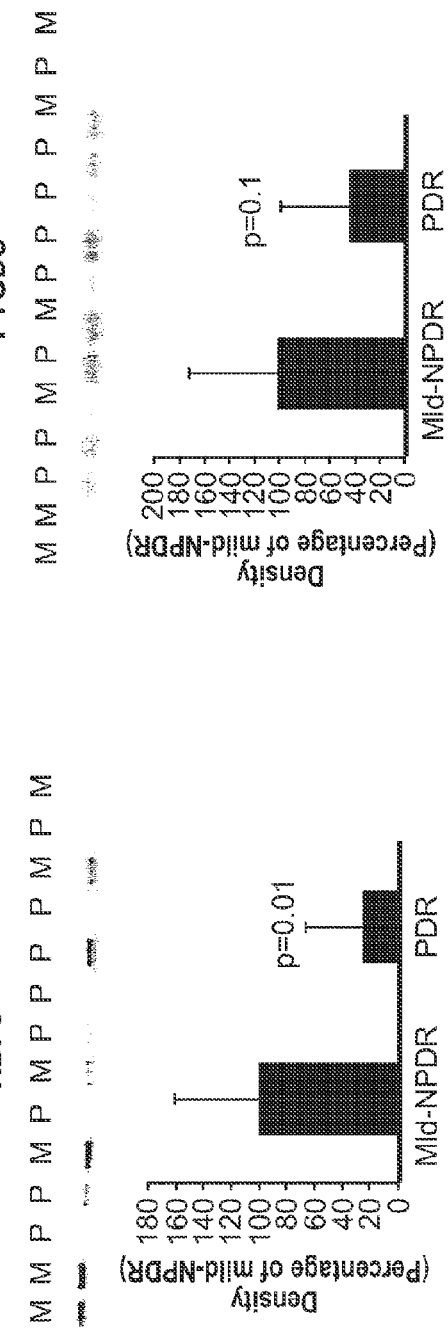
Figure 11C:
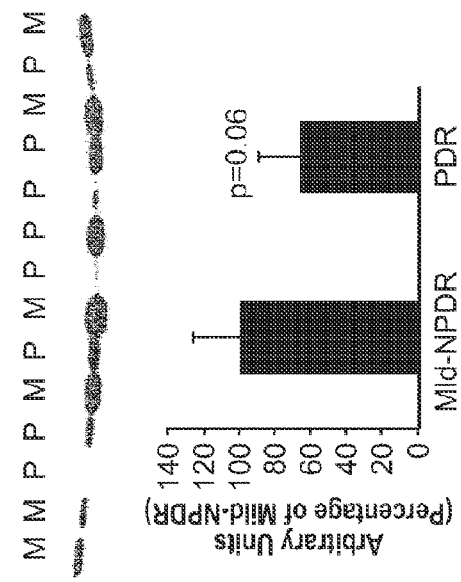

Western Blot confirmed that RBP3 protein levels are significantly higher in vitreous of Medalists without PDR than in vitreous from Medalists with PDR (pval=0.01; FIG. 11). Cystatin C protein levels showed a similar trend (pval=0.06). Although the difference in PTGDS levels between both groups was not statistically significant, we decided to pursue this protein as well, since it belongs to the lipocalin superfamily (as does RBP3), and can bind to the same substrates.

CST3 is universally expressed. We confirmed that CST3 is detected in mouse retina protein extracts by Western blot (data not shown). RBP3 is secreted by the retinal photoreceptor cells (RPE), and thus, it could play a role in retinal endothelial cells and pericytes even when those cells do not express RBP3.

RBP3 was also quantified in the vitreous of Medalists with no-mild NPDR, active PDR or quiescent PDR by proteomics analysis. No to mild NPDR is as described above. "Quiescent PDR" corresponds to ETDRS severity level >60, characterized by the presence of neovascularization, fibrous proliferation, or panretinal laser photocoagulation scars.

Figure 12:
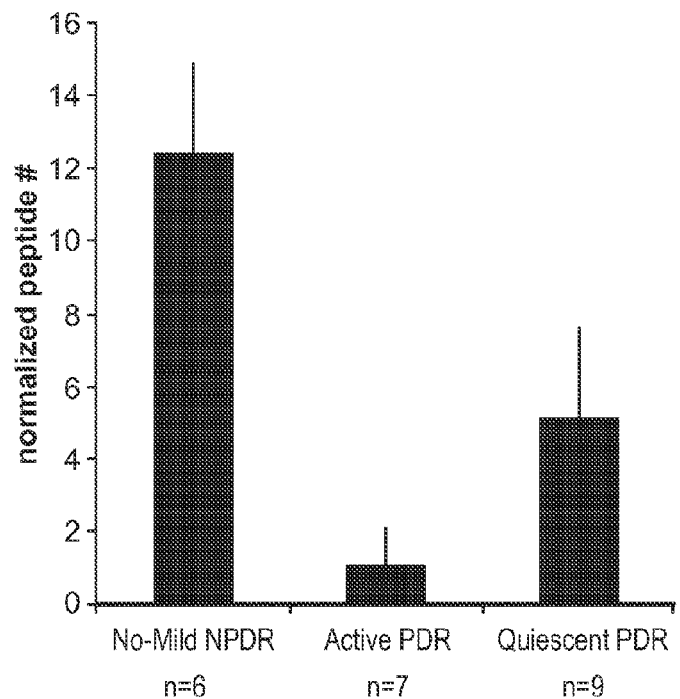
FIG. 12 is a histogram with the values of RBP3 protein levels in vitreous of Medalists without PDR versus in vitreous from Medalists with active PDR or quiescent PDR, as measured via Western blots.

The results, which are shown in FIG. 12, indicate that the level of RBP3 is high in Medalists with no DR, low in Medalists with active PDR and present at an intermediary level in Medalists with quiescent PDR. This data shows that the Medalist patients without PDR have retained high levels of RBP3 despite a long duration of type1 diabetes.

Figure 13:
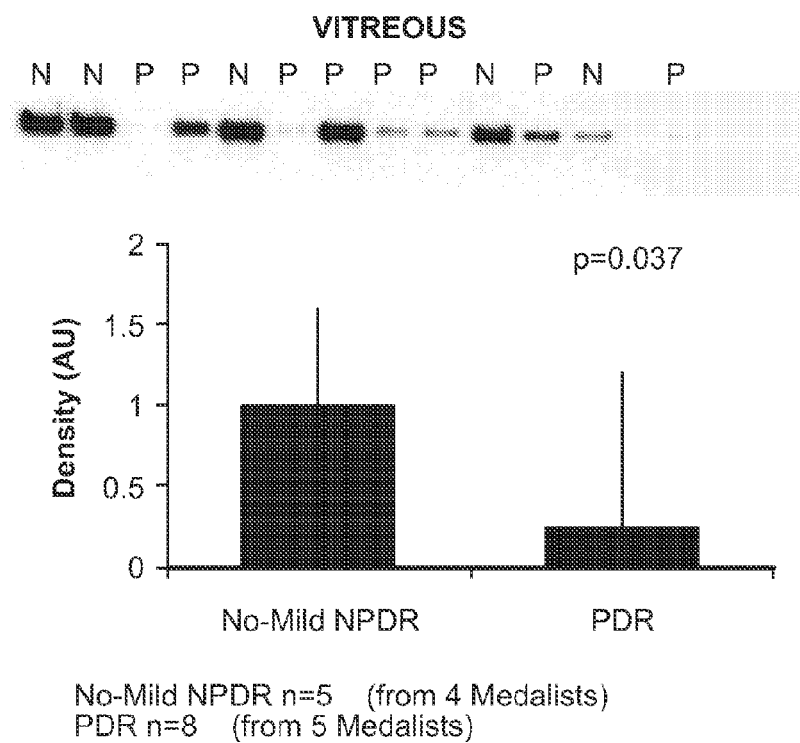
FIG. 13 represents a Western blot (A) and a diagram (B) showing the levels of RBP3 in vitreous of Medalists with no to mild NPDR ("N") and Medalists with PDR ("PDR").

The level of RBP3 was also determined in the vitreous of Medalists with no to mild NPDR and compared to that in Medalists with PDR using proteomics analysis. The results, which are shown in FIG. 13, indicate that the level of RBP3 is higher in Medalists with no to mild NPDR relative to that in Medalists with PDR.

Example 7

RBP3 Protein Levels are Higher in the Retina of Medalists with Mild NPDR Relative to that in Medalists with PDR The level of RBP3 was also determined in the retina of Medalists with mild NPDR and Medalists with PDR. The assay was conducted as follows: 10 ug of protein were loaded onto a 4-20% gel (Biorad) and transferred to a PVDF membrane (Immobilon-P) and immunoblotted as described above.

Figure 14A:
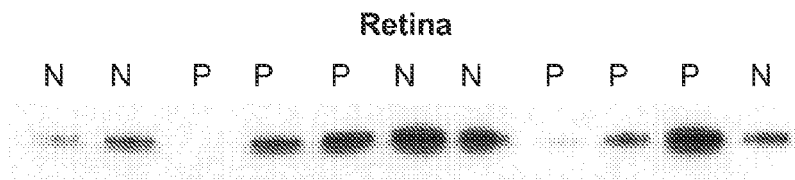
FIG. 14 A & B represents a Western blot (A) and a diagram (B) showing the levels of RBP3 in retina of Medalists with mild NPDR ("N") and Medalists with PDR ("P").
Figure 14B:
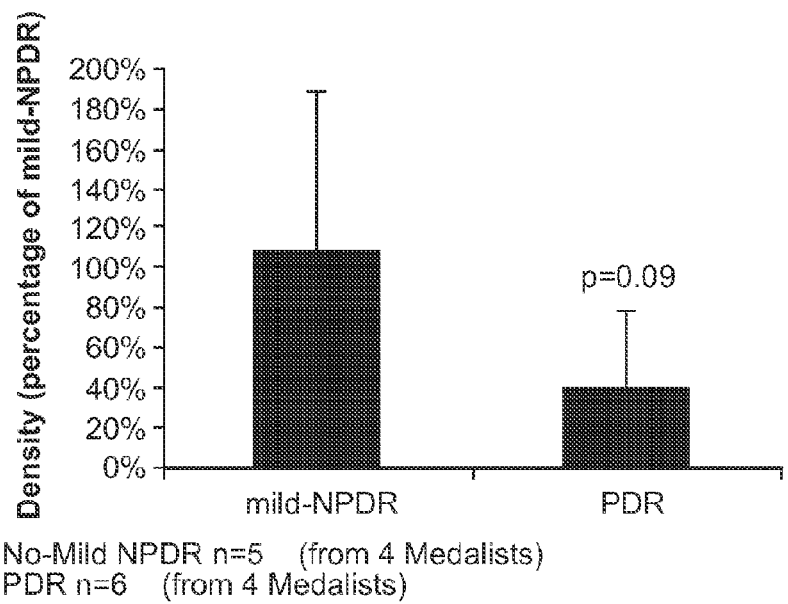

The results, which are shown in FIG. 14, indicate that the level of RBP3 follows the same trend as the vitreous, i.e. higher RBP3 in the retina of Medalists with mild NPDR relative to that in Medalists with PDR.

Example 8

RBP3 is Expressed in Human Plasma

This Example describes that plasma from healthy human subjects contain detectable levels of RBP3. This was surprising, as RBP3 was so far believed to be present only in the eye.

Human plasma was obtained from control subjects from the Medalist study at the Joslin Diabetes Center. A blood sample was extracted by venipuncture using standard CLIA protocol after patient consent was obtained using a 10 mL EDTA tube by a trained phlebotomist. This was then centrifuged at 4 degrees centigrade for 10 mins at 4000 rpm. After this process the supernatant (plasma) was aliquotted off into 100 mL samples and stored at −80 centigrade. The human plasma was serum albumin and IgG depleted using Pierce kit (89875) following the manufacturers instructions. Equal volumes (20 ul) were loaded on a gel and immunoblotted as described above.

Figure 15:
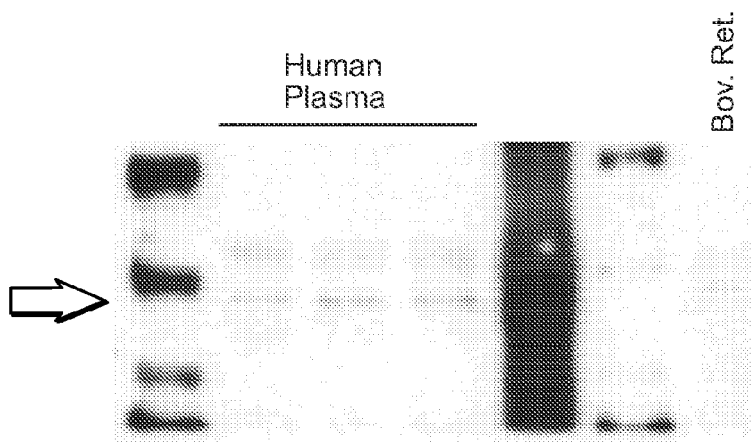
FIG. 15 is a Western blot showing the presence of RBP3 in human plasma.

The results, which are shown in FIG. 15, indicate that RBP3 is present in human plasma.

Example 9

RBP3 Protect Cells from High Glucose Exposure

This Example describes that human RBP3 protects endothelial cells from being activated by high glucose exposure, as shown in an endothelial migration assay.

Human RBP3 was prepared as follows: hRBP3 ORF containing plasmid was purchased from Origene (RC08063), transfected into HEK 293 cells using Fugene HD (Promega), the cells lysed and RBP3 was bound to M2 resin (Sigma, Aldrich) and eluted using 1× Flag peptide (Sigma) following the manufacturer's instructions. The purified peptide was confirmed by immunoblotting against the DDK tag, and a 137 kDa band was confirmed.

The migration assays were performed as follows: bovine retinal endothelial cells (BREC) were isolated as previously described (King et al, *J Clin Invest.* 1983; 71(4):974-979). $3 \times 10^4$ per well were plated in a 24 well plate. The following day, a scratch was made, the cells rinsed off with saline to remove floating cells, and incubated with different conditions (low glucose=5.6 mM, high glucose=25.6 mM D-glucose, Vehicle=TBS buffer, RBP3=1:100 dilution). The width of this gap was measured at 0 and 4 hours in the corresponding conditions, two pictures of each gap were taken at each time point and the average was used. Four wells were plated for each condition. Statistics were done with excel (student ttest).

Figure 16:
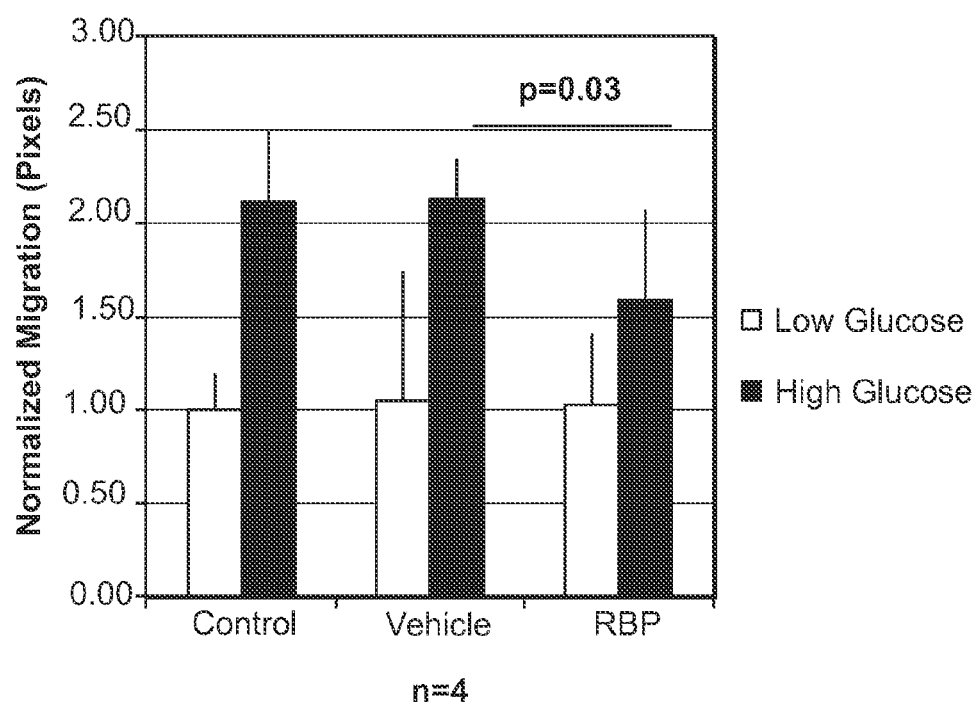
FIG. 16 is a diagram showing the number of endothelial cells that have migrated in the migration assay, following exposure to low or high glucose concentrations and no treatment, treatment with vehicle alone and treatment with RBP3.

The results, which are shown in FIG. 16, indicate that RBP3 prevents the endothelial cells from migrating in response to the high glucose concentration, thereby indicating that RBP3 protects endothelial cells from the toxic effects of a high glucose environment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Incorporation by Reference

The disclosure of each and every publication, including US and foreign patent and pending patent applications, referred to herein is specifically incorporated by reference herein in its entirety.

What is claimed is:

1. A method for treating diabetic retinopathy (DR) in a subject, the method comprising selecting a subject with DR and administering to the subject a therapeutically effective amount of a therapeutic agent comprising retinol binding protein 3 (RBP3).

2. The method of claim 1, wherein the therapeutic agent is administered systemically.

3. The method of claim 1, wherein the therapeutic agent is administered locally to the eye.

4. The method of claim 3, wherein the therapeutic agent is injected into the vitreous of the eye.

5. The method of claim 1, further determining the effectiveness of the treatment by measuring the level of RBP3 in the subject.

* * * * *

SEQUENCE LISTING

```
<160> NUMBER OF SEQ ID NOS: 4

<210> SEQ ID NO 1
<211> LENGTH: 4289
<212> TYPE: DNA
<213> ORGANISM: Homo sapiens

<400> SEQUENCE: 1
tgtccaccag ctgagaagga caagggcgga aggcagctgc acagagcagg gccacggcct      60
tgcacacagt ccagggagct tttgtgcagg agccaggcct cccctgggt ccccatgatg      120 agagaatggg ttctgctcat gtccgtgctg ctctgtggcc tggctggccc cacacacctg     180
ttccagccaa gcctggtgct ggacatggcc aaggtcctct tggataacta ctgcttcccg     240
gagaacctgc tgggcatgca ggaagccatc cagcaggcca tcaagagcca tgagattctg     300
agcatctcag acccgcagac gctggccagt gtgctgacag ccggggtgca gagctccctg     360
aacgatcctc gcctggtcat ctcctatgag cccagcaccc ccgagcctcc cccacaagtc     420
ccagcactca ccagcctctc agaagaggaa ctgcttgcct ggctgcaaag gggcctccgc     480
catgaggttc tggagggtaa tgtgggctac ctgcgggtgg acagcgtccc gggccaggag     540
gtgctgagca tgatggggga gttcctggtg gcccacgtgt gggggaatct catgggcacc     600
tccgccttag tgctggatct ccggcactgc acaggaggcc aggtctctgg cattccctac     660
atcatctcct acctgcaccc agggaacacc atcctgcacg tggacactat ctacaaccgc     720
ccctccaaca ccaccacgga gatctggacc ttgcccagg tcctgggaga aaggtacggt     780
gccgacaagg atgtggtggt cctcaccagc agccagacca ggggcgtggc cgaggacatc     840
gcgcacatcc ttaagcagat gcgcagggcc atcgtggtgg gcgagcggac tggggagggg     900
gccctggacc tccggaagct gaggataggc gagtctgact tcttcttcac ggtgcccgtg     960
tccaggtccc tggggcccct tggtggaggc agccagacgt gggagggcag cggggtgctg     1020
ccctgtgtgg ggactccggc cgagcaggcc ctggagaaag ccctggccat cctcactctg     1080
cgcagcgccc ttccaggggt agtccactgc ctccaggagg tcctgaagga ctactacacg     1140
ctggtggacc gtgtgcccac cctgctgcag cacttggcca gcatggactt ctccacggtg     1200
gtctccgagg aagatctggt caccaagctc aatgccggcc tgcaggctgc gtctgaggat     1260
```

```
cccaggctcc tggtgcgagc catcgggccc acagaaactc cttcttggcc cgcgcccgac   1320
gctgcagccg aagactcacc aggggtggcc ccagagttgc ctgaggacga ggctatccgg   1380
caagcactgg tggactctgt gttccaggtg tcggtgctgc aggcaatgt gggctacctg    1440 cgcttcgata gttttgctga cgcctccgtc ctgggtgtgt tggccccata tgtcctgcgc   1500
caggtgtggg agccgctaca ggacacggag cacctcatca tggacctgcg ccacaaccct   1560
ggagggccat cctctgctgt gcccctgctc ctgtcctact tccagggccc tgaggccggc   1620
cccgtgcacc tcttcaccac ctatgatcgc cgcaccaaca tcacgcagga gcacttcagc   1680
cacatggagc tcccgggccc acgctacagc acccaacgtg gggtgtatct gctcaccagc   1740
caccgcaccg ccacggccgc ggaggagttc gccttcctta tgcagtcgct gggctgggcc   1800
acactggtag gtgagatcac cgcgggcaac ctgctgcaca cccgcacggt gccgctgctg   1860
gacacacccg aaggcagcct cgcgctcacc gtgccggtcc tcaccttcat cgacaatcac   1920
ggcgaggcct ggctgggtgg tggagtggtg cccgatgcca tcgtgctggc cgaggaggcc   1980
ctggacaaag cccaggaagt gctggagttc accaaagcc tggggccctt ggtggagggc    2040
acagggcacc tgctggaggc ccactatgct cggccagagg tcgtggggca gaccagtgcc   2100
ctcctgcggg ccaagctggc ccaggcgcc taccgcacag ctgtggactt ggagtctctg     2160
gcctctcagc tcacagcaga cctccaggag gtgtctgggg accaccgctt gctagtgttc   2220
cacagccctg gcgagctggt ggtagaggaa gcacccccac cacccctgc tgtccctct     2280 ccagaggagc tcacctacct tattgaggcc ctgttcaaga cagaggtgct gcccggccag   2340
ctgggctacc tgcgttttga cgccatggct gaactggaga cagtgaaggc cgtggggcca   2400
cagctggtgc ggctggtatg caacagctg gtggacacgg ctgcgctggt gatcgacctg     2460
cgctacaacc ctggcagcta ctccacggcc atcccgctgc tctgctccta cttctttgag   2520
gcagagcccc gccagcacct gtattctgtc tttgacaggg ccacctcaaa agtcacggag   2580
gtgtggacct tgccccaggt cgccggccag cgctacggct cacacaagga cctctacatc   2640
ctgatgagcc acaccagtgg ctctgcggcc gaggcctttg cacacaccat gcaggacctg   2700
cagcgggcca cggtcattgg ggagcccacg gccgaggcg cactctctgt gggcatctac    2760
caggtgggca gcagccccttt atatgcatcc atgcccaccc agatggccat gagtgccacc   2820
acaggcaagg cctgggacct ggctggtgtg gagcccgaca tcactgtgcc catgagcgaa   2880 gcccttttcca tagcccagga catagtggct ctgcgtgcca aggtgcccac ggtgctgcag   2940
acggccggga agctggtggc tgataactat gcctctgccg agctgggggc caagatggcc   3000
accaaactga gcggtctgca gagccgctac tccagggtga cctcagaagt ggccctagcc   3060
gagatcctgg gggctgacct gcagatgctc tccggagacc cacacctgaa ggcagcccat   3120
atccctgaga atgccaagga ccgcattcct ggaattgtgc ccatgcagat cccttcccct   3180
gaagtatttg aagagctgat caagtttttcc ttccacacta acgtgcttga ggacaacatt   3240
ggctacttga ggtttgacat gtttgggac ggtgagctgc tcacccaggt ctccaggctg    3300
ctggtggagc acatctggaa gaagatcatg cacacggatg ccatgatcat cgacatgagg   3360
ttcaacatcg gtgccccac atcctccatt cccatcttgt gctcctactt ctttgatgaa    3420
ggccctccag ttctgctgga caagatctac agccggcctg atgactctgt cagtgaactc   3480
tggacacacg cccaggttgt aggtgaacgc tatggctcca agaagagcat ggtcattctg   3540
accagcagtg tgacgccgg caccgcggag gagttcacct atatcatgaa gaggctgggc   3600
cgggccctgg tcattgggga ggtgaccagt ggggggctgcc agccaccaca gacctaccac  3660
```

-continued

```
gtggatgaca ccaacctcta cctcactatc cccacggccc gttctgtggg ggcctcggat    3720
ggcagctcct gggaaggggt gggggtgaca ccccatgtgg ttgtccctgc agaagaggct    3780
ctcgccaggg ccaaggagat gctccagcac aaccagctga gggtgaagcg gagcccaggc    3840
ctgcaggacc acctgtaggg aagggccccca taggcagagc cccagggcag acagaacctc    3900
tgggacacac accaagggca ctcctgcagg tggcccggcc tgaggttccc aggagcagca    3960
aaggggcctg ctgagctctg gttaggttac agctggaggt gtgtatatat acacacacac    4020
acatgtatat acacatatat atgtgtatgt atatatgt atatatatat ggctttccaa      4080
taaccaccta aatttaaca aaggttcctt ctaagtggta gaacttgggg tggtattttt     4140
accttccttc ttcatacttt gctctttttc ttaaatactc attaatgtgc atatatcatt    4200
attttcagat gcagctatca ttattccaaa atacaaaata aagaagataa aataaattat   4260
atacccgagc cattaaaaaa aaaaaaaaa                                      4289
```

<210> SEQ ID NO 2
<211> LENGTH: 1247
<212> TYPE: PRT
<213> ORGANISM: Homo sapiens

<400> SEQUENCE: 2

```
Met Met Arg Glu Trp Val Leu Leu Met Ser Val Leu Leu Cys Gly Leu
1               5                   10                  15

Ala Gly Pro Thr His Leu Phe Gln Pro Ser Leu Val Leu Asp Met Ala
            20                  25                  30

Lys Val Leu Leu Asp Asn Tyr Cys Phe Pro Glu Asn Leu Gly Met
        35                  40                  45

Gln Glu Ala Ile Gln Gln Ala Ile Lys Ser His Glu Ile Leu Ser Ile
    50                  55                  60

Ser Asp Pro Gln Thr Leu Ala Ser Val Leu Thr Ala Gly Val Gln Ser
65                  70                  75                  80

Ser Leu Asn Asp Pro Arg Leu Val Ile Ser Tyr Glu Pro Ser Thr Pro
                85                  90                  95

Glu Pro Pro Pro Gln Val Pro Ala Leu Thr Ser Leu Ser Glu Glu Glu
            100                 105                 110

Leu Leu Ala Trp Leu Gln Arg Gly Leu Arg His Glu Val Leu Glu Gly
        115                 120                 125

Asn Val Gly Tyr Leu Arg Val Asp Ser Val Pro Gly Gln Glu Val Leu
    130                 135                 140

Ser Met Met Gly Glu Phe Leu Val Ala His Val Trp Gly Asn Leu Met
145                 150                 155                 160

Gly Thr Ser Ala Leu Val Leu Asp Leu Arg His Cys Thr Gly Gly Gln
                165                 170                 175

Val Ser Gly Ile Pro Tyr Ile Ile Ser Tyr Leu His Pro Gly Asn Thr
            180                 185                 190

Ile Leu His Val Asp Thr Ile Tyr Asn Arg Pro Ser Asn Thr Thr Thr
        195                 200                 205

Glu Ile Trp Thr Leu Pro Gln Val Leu Gly Glu Arg Tyr Gly Ala Asp
    210                 215                 220

Lys Asp Val Val Val Leu Thr Ser Ser Gln Thr Arg Gly Val Ala Glu
225                 230                 235                 240

Asp Ile Ala His Ile Leu Lys Gln Met Arg Arg Ala Ile Val Val Gly
                245                 250                 255
```

```
Glu Arg Thr Gly Gly Ala Leu Asp Leu Arg Lys Leu Arg Ile Gly
                260                 265                 270

Glu Ser Asp Phe Phe Thr Val Pro Val Ser Arg Ser Leu Gly Pro
            275                 280                 285

Leu Gly Gly Gly Ser Gln Thr Trp Glu Gly Ser Gly Val Leu Pro Cys
290                 295                 300

Val Gly Thr Pro Ala Glu Gln Ala Leu Glu Lys Ala Leu Ala Ile Leu
305                 310                 315                 320

Thr Leu Arg Ser Ala Leu Pro Gly Val Val His Cys Leu Gln Glu Val
                325                 330                 335

Leu Lys Asp Tyr Tyr Thr Leu Val Asp Arg Val Pro Thr Leu Leu Gln
                340                 345                 350

His Leu Ala Ser Met Asp Phe Ser Thr Val Val Ser Glu Glu Asp Leu
                355                 360                 365

Val Thr Lys Leu Asn Ala Gly Leu Gln Ala Ala Ser Glu Asp Pro Arg
370                 375                 380

Leu Leu Val Arg Ala Ile Gly Pro Thr Glu Thr Pro Ser Trp Pro Ala
385                 390                 395                 400

Pro Asp Ala Ala Ala Glu Asp Ser Pro Gly Val Ala Pro Glu Leu Pro
                405                 410                 415

Glu Asp Glu Ala Ile Arg Gln Ala Leu Val Asp Ser Val Phe Gln Val
                420                 425                 430

Ser Val Leu Pro Gly Asn Val Gly Tyr Leu Arg Phe Asp Ser Phe Ala
            435                 440                 445

Asp Ala Ser Val Leu Gly Val Leu Ala Pro Tyr Val Leu Arg Gln Val
            450                 455                 460

Trp Glu Pro Leu Gln Asp Thr Glu His Leu Ile Met Asp Leu Arg His
465                 470                 475                 480

Asn Pro Gly Gly Pro Ser Ser Ala Val Pro Leu Leu Leu Ser Tyr Phe
                485                 490                 495

Gln Gly Pro Glu Ala Gly Pro Val His Leu Phe Thr Thr Tyr Asp Arg
                500                 505                 510

Arg Thr Asn Ile Thr Gln Glu His Phe Ser His Met Glu Leu Pro Gly
            515                 520                 525

Pro Arg Tyr Ser Thr Gln Arg Gly Val Tyr Leu Leu Thr Ser His Arg
            530                 535                 540

Thr Ala Thr Ala Ala Glu Glu Phe Ala Phe Leu Met Gln Ser Leu Gly
545                 550                 555                 560

Trp Ala Thr Leu Val Gly Glu Ile Thr Ala Gly Asn Leu Leu His Thr
                565                 570                 575

Arg Thr Val Pro Leu Leu Asp Thr Pro Glu Gly Ser Leu Ala Leu Thr
                580                 585                 590

Val Pro Val Leu Thr Phe Ile Asp Asn His Gly Glu Ala Trp Leu Gly
                595                 600                 605

Gly Gly Val Val Pro Asp Ala Ile Val Leu Ala Glu Glu Ala Leu Asp
610                 615                 620

Lys Ala Gln Glu Val Leu Glu Phe His Gln Ser Leu Gly Ala Leu Val
625                 630                 635                 640

Glu Gly Thr Gly His Leu Leu Glu Ala His Tyr Ala Arg Pro Glu Val
                645                 650                 655

Val Gly Gln Thr Ser Ala Leu Leu Arg Ala Lys Leu Ala Gln Gly Ala
                660                 665                 670

Tyr Arg Thr Ala Val Asp Leu Glu Ser Leu Ala Ser Gln Leu Thr Ala
```

-continued

```
                675                 680                 685
Asp Leu Gln Glu Val Ser Gly Asp His Arg Leu Leu Val Phe His Ser
690                 695                 700
Pro Gly Glu Leu Val Val Glu Ala Pro Pro Pro Pro Ala Val
705                 710                 715                 720
Pro Ser Pro Glu Glu Leu Thr Tyr Leu Ile Glu Ala Leu Phe Lys Thr
            725                 730                 735
Glu Val Leu Pro Gly Gln Leu Gly Tyr Leu Arg Phe Asp Ala Met Ala
                740                 745                 750
Glu Leu Glu Thr Val Lys Ala Val Gly Pro Gln Leu Val Arg Leu Val
                755                 760                 765
Trp Gln Gln Leu Val Asp Thr Ala Ala Leu Val Ile Asp Leu Arg Tyr
770                 775                 780
Asn Pro Gly Ser Tyr Ser Thr Ala Ile Pro Leu Leu Cys Ser Tyr Phe
785                 790                 795                 800
Phe Glu Ala Glu Pro Arg Gln His Leu Tyr Ser Val Phe Asp Arg Ala
                805                 810                 815
Thr Ser Lys Val Thr Glu Val Trp Thr Leu Pro Gln Val Ala Gly Gln
                820                 825                 830
Arg Tyr Gly Ser His Lys Asp Leu Tyr Ile Leu Met Ser His Thr Ser
                835                 840                 845
Gly Ser Ala Ala Glu Ala Phe Ala His Thr Met Gln Asp Leu Gln Arg
850                 855                 860
Ala Thr Val Ile Gly Glu Pro Thr Ala Gly Ala Leu Ser Val Gly
865                 870                 875                 880
Ile Tyr Gln Val Gly Ser Pro Leu Tyr Ala Ser Met Pro Thr Gln
                885                 890                 895
Met Ala Met Ser Ala Thr Thr Gly Lys Ala Trp Asp Leu Ala Gly Val
                900                 905                 910
Glu Pro Asp Ile Thr Val Pro Met Ser Glu Ala Leu Ser Ile Ala Gln
                915                 920                 925
Asp Ile Val Ala Leu Arg Ala Lys Val Pro Thr Val Leu Gln Thr Ala
930                 935                 940
Gly Lys Leu Val Ala Asp Asn Tyr Ala Ser Ala Glu Leu Gly Ala Lys
945                 950                 955                 960
Met Ala Thr Lys Leu Ser Gly Leu Gln Ser Arg Tyr Ser Arg Val Thr
                965                 970                 975
Ser Glu Val Ala Leu Ala Glu Ile Leu Gly Ala Asp Leu Gln Met Leu
                980                 985                 990
Ser Gly Asp Pro His Leu Lys Ala Ala His Ile Pro Glu Asn Ala Lys
                995                 1000                1005
Asp Arg Ile Pro Gly Ile Val Pro Met Gln Ile Pro Ser Pro Glu
        1010                1015                1020
Val Phe Glu Glu Leu Ile Lys Phe Ser Phe His Thr Asn Val Leu
        1025                1030                1035
Glu Asp Asn Ile Gly Tyr Leu Arg Phe Asp Met Phe Gly Asp Gly
        1040                1045                1050
Glu Leu Leu Thr Gln Val Ser Arg Leu Leu Val Glu His Ile Trp
        1055                1060                1065
Lys Lys Ile Met His Thr Asp Ala Met Ile Ile Asp Met Arg Phe
        1070                1075                1080
Asn Ile Gly Gly Pro Thr Ser Ser Ile Pro Ile Leu Cys Ser Tyr
        1085                1090                1095
```

| | | | | | | | | | | | |
|---|---|---|---|---|---|---|---|---|---|---|---|
| Phe | Phe | Asp | Glu | Gly | Pro | Pro | Val | Leu | Leu | Asp | Lys | Ile | Tyr | Ser |
| | 1100 | | | | 1105 | | | | | 1110 | |

Phe Phe Asp Glu Gly Pro Pro Val Leu Leu Asp Lys Ile Tyr Ser
    1100                1105                    1110

Arg Pro Asp Asp Ser Val Ser Glu Leu Trp Thr His Ala Gln Val
    1115                1120                    1125

Val Gly Glu Arg Tyr Gly Ser Lys Lys Ser Met Val Ile Leu Thr
    1130                1135                    1140

Ser Ser Val Thr Ala Gly Thr Ala Glu Glu Phe Thr Tyr Ile Met
    1145                1150                    1155

Lys Arg Leu Gly Arg Ala Leu Val Ile Gly Glu Val Thr Ser Gly
    1160                1165                    1170

Gly Cys Gln Pro Pro Gln Thr Tyr His Val Asp Asp Thr Asn Leu
    1175                1180                    1185

Tyr Leu Thr Ile Pro Thr Ala Arg Ser Val Gly Ala Ser Asp Gly
    1190                1195                    1200

Ser Ser Trp Glu Gly Val Gly Val Thr Pro His Val Val Val Pro
    1205                1210                    1215

Ala Glu Glu Ala Leu Ala Arg Ala Lys Glu Met Leu Gln His Asn
    1220                1225                    1230

Gln Leu Arg Val Lys Arg Ser Pro Gly Leu Gln Asp His Leu
    1235                1240                    1245

<210> SEQ ID NO 3
<211> LENGTH: 1507
<212> TYPE: DNA
<213> ORGANISM: Homo sapiens

<400> SEQUENCE: 3

```
tgggcggcgg ctgaggcgcg tgctctcgcg tggtcgctgg gtctgcgtct tcccgagcca      60
gtgtgctgag ctctccgcgt cgcctctgtc gcccgcgcct ggcctaccgc ggcactcccg     120
gctgcacgct ctgcttggcc tcgccatgcc ggtggacctc agcaagtggt ccggggccctt    180
gagcctgcaa gaagtggacg agcagccgca gcacccgctg catgtcacct acgccggggc     240
ggcggtggac gagctgggca agtgctgac gcccacccag gttaagaata gacccaccag     300
catttcgtgg gatggtcttg attcagggaa gctctacacc ttggtcctga cagacccgga    360
tgctcccagc aggaaggatc ccaaatacag agaatggcat catttcctgg tggtcaacat     420
gaagggcaat gacatcagca gtggcacagt cctctccgat tatgtgggct cggggcctcc     480
caagggcaca ggcctccacc gctatgtctg gctggtttac gagcaggaca ggccgctaaa     540
gtgtgacgag cccatcctca gcaaccgatc tggagaccac cgtggcaaat tcaaggtggc     600
gtccttccgt aaaaagtatg agctcagggc cccggtggct ggcacgtgtt accaggccga     660
gtgggatgac tatgtgccca aactgtacga gcagctgtct gggaagtagg gggttagctt     720
ggggacctga actgtcctgg aggccccaag ccatgttccc cagttcagtg ttgcatgtat     780
aatagatttc tcctcttcct gcccccttg gcatgggtga cctgacca gtcagatggt      840
agttgagggt gacttttcct gctgcctggc ctttataatt ttactcactc actctgattt     900
atgttttgat caaatttgaa cttcattttg ggggtattt tggtactgtg atggggtcat      960
caaattatta atctgaaaat agcaacccag aatgtaaaaa agaaaaaact ggggggaaaa    1020
agaccaggtc tacagtgata gagcaaagca tcaaagaatc tttaagggag gtttaaaaaa    1080
aaaaaaaaaa aaaagattg gttgcctctg cctttgtgat cctgagtcca gaatggtaca    1140
caatgtgatt ttatggtgat gtcactcacc tagacaacca gaggctggca ttgaggctaa    1200
```

```
cctccaacac agtgcatctc agatgcctca gtaggcatca gtatgtcact ctggtccctt    1260
taaagagcaa tcctggaaga agcaggaggg agggtggctt tgctgttgtt gggacatggc    1320
aatctagacc ggtagcagcg ctcgctgaca gcttgggagg aaacctgaga tctgtgtttt    1380
ttaaattgat cgttcttcat gggggtaaga aaagctggtc tggagttgct gaatgttgca    1440
ttaattgtgc tgtttgcttg tagttgaata aaaatagaaa cctgaatgaa gaaaaaaaaa    1500
aaaaaaa                                                              1507

<210> SEQ ID NO 4
<211> LENGTH: 187
<212> TYPE: PRT
<213> ORGANISM: Homo sapiens

<400> SEQUENCE: 4

Met Pro Val Asp Leu Ser Lys Trp Ser Gly Pro Leu Ser Leu Gln Glu
1               5                   10                  15

Val Asp Glu Gln Pro Gln His Pro Leu His Val Thr Tyr Ala Gly Ala
            20                  25                  30

Ala Val Asp Glu Leu Gly Lys Val Leu Thr Pro Thr Gln Val Lys Asn
        35                  40                  45

Arg Pro Thr Ser Ile Ser Trp Asp Gly Leu Asp Ser Gly Lys Leu Tyr
    50                  55                  60

Thr Leu Val Leu Thr Asp Pro Asp Ala Pro Ser Arg Lys Asp Pro Lys
65                  70                  75                  80

Tyr Arg Glu Trp His His Phe Leu Val Val Asn Met Lys Gly Asn Asp
                85                  90                  95

Ile Ser Ser Gly Thr Val Leu Ser Asp Tyr Val Gly Ser Gly Pro Pro
            100                 105                 110

Lys Gly Thr Gly Leu His Arg Tyr Val Trp Leu Val Tyr Glu Gln Asp
        115                 120                 125

Arg Pro Leu Lys Cys Asp Glu Pro Ile Leu Ser Asn Arg Ser Gly Asp
    130                 135                 140

His Arg Gly Lys Phe Lys Val Ala Ser Phe Arg Lys Lys Tyr Glu Leu
145                 150                 155                 160

Arg Ala Pro Val Ala Gly Thr Cys Tyr Gln Ala Glu Trp Asp Asp Tyr
                165                 170                 175

Val Pro Lys Leu Tyr Glu Gln Leu Ser Gly Lys
            180                 185
```